(12) United States Patent
Aoki et al.

(10) Patent No.: US 7,514,416 B2
(45) Date of Patent: Apr. 7, 2009

(54) INTERFERON ALPHA AND ANTISENSE K-RAS RNA COMBINATION GENE THERAPY

(75) Inventors: Kazunori Aoki, Tokyo (JP); Teruhiko Yoshida, Tokyo (JP)

(73) Assignee: Japan Health Sciences Foundation, Tokyo (JP)

(*) Notice: Subject to any disclaimer, the term of this patent is extended or adjusted under 35 U.S.C. 154(b) by 0 days.

(21) Appl. No.: 11/114,088

(22) Filed: Apr. 26, 2005

(65) Prior Publication Data

US 2005/0260167 A1 Nov. 24, 2005

Related U.S. Application Data

(60) Provisional application No. 60/565,526, filed on Apr. 27, 2004.

(51) Int. Cl.
*A61K 31/70* (2006.01)
(52) U.S. Cl. .............. 514/44; 536/23.5; 435/320.1
(58) Field of Classification Search .............. None
See application file for complete search history.

(56) References Cited

OTHER PUBLICATIONS

Wolff et al, Invest New Drugs 2000; 18:43-56.*
Verma, Sep. 1997, Nature, vol. 389, pp. 239-242.*
Crystal, 1995, Science, vol. 270, p. 404-410.*
Harrington et al. 2001; J. Urol., vol. 166, 1220-1233.*
Rainov et al. 2001;Curr. Gene Ther., vol. 1, 367-383.*
Sakai et al, Biochem Biophys Res Commun 1995;4;217:393-401.*
Miura et al, Mole Ther 2003;7:S417.*
Solorzano et al, Clin Cancer Res 2003;9:1858-67.*
Nakano et al, Mole Ther 2001;3:491-9.*
Sabaawy et al, Int J Oncol 1999;14:1143-51.*
Haller, "Future directions in the treatment of pancreatic cancer", Seminars in Oncology, vol. 29, pp. 31-39 (2002).
Ryan et al., "Management of locally advanced adenocarcinoma of the pancreas", Hematol Oncol Clin North Am, vol. 16, pp. 95-103 (2002).
Kaufman et al., "Immunotherapy for pancreatic cancer: current concepts", Hematol Oncol Clin North Am, vol. 16, pp. 159-197 (2002).
Pfeffer et al., "Biological properties of recombinant α-interferons: 40th anniversary of the discovery of interferons", Cancer Res, vol. 58, pp. 2489-2499 (1998).
Gutterman, "Cytokine therapeutics: lessons from interferon α", Proc Natl Acad Sci USA, vol. 91, pp. 1198-1205 (1994).
Matsubara et al., "Antiproliferative effects of natural human tumor necrosis factor- α, interferon-α, and interferon-γ on human pancreatic carcinoma cell lines", Int J Pancreatol, vol. 8, pp. 235-243 (1991).
Watanabe et al., "Anti-proliferative effect on human pancreatic cancer cells of natural human tumour necrosis factor-β combined with natural human interferon-α or interferon- γ", The Journal of International Medical Research, vol. 20, pp. 112-120 (1992).
Recchia et al., "Advanced carcinoma of the pancreas: phase II study of combined chemotherapy, β-interferon, and retinoids", Am J Clin Oncol, vol. 21, pp. 275-278 (1998).

Nukui et al., "Interferon-based adjuvant chemoradiation therapy improves survival after pancreaticoduodenectomy for pancreatic adenocarcinoma", Am J Surg, vol. 179, pp. 367-371 (2000).
MacDonald et al., "A phase II trial of etoposide, leucovorin, 5-FU, and interferon alpha 2b (ELFI) + G-CSF for patients with pancreatic adenocarcinoma: a Southwest Oncology Group study (SWOG 9413)", Invest New Drugs, vol. 18, pp. 269-273 (2000).
David et al., "A phase II trial of 5-fluorouracil, leucovorin, and interferon alpha 2A (IFN- α 2a) in metastatic pancreatic carcinoma: a Penn Cancer Clinical Trials Group (PCCTG) trial", Am J Clin Oncol, vol. 23, pp. 37-39 (2000).
Ahmed et al., "Selective expression of nonsecreted interferon by an adenoviral vector confers antiproliferative and antiviral properties and causes reduction of tumor growth in nude mice", J Interferon Cytokine Res, vol. 21, pp. 399-408 (2001).
Zhang et al., "Treatment of a human breast cancer xenograft with an adenovirus vector containing an interferon gene results in rapid regression due to viral oncolysis and gene therapy", Proc Natl Acad Sci USA, vol. 93, pp. 4513-4518 (1996).
Ahmed et al., "In vivo tumor suppression by adenovirus-mediated interferon α2b gene delivery", Hum Gene Ther, vol. 10, pp. 77-84 (1999).
Santodonato et al., "Antitumor activity of recombinant adenoviral vectors expressing murine IFN-α in mice injected with metastatic IFN-resistant tumor cells", Cancer Gene Ther, vol. 8, pp. 63-72 (2001).
Tuting et al. Interferon- α gene therapy for cancer: retroviral transduction of fibroblasts and particle-mediated transfection of tumor cells are both effective strategies for gene delivery in murine tumor models, Gene Ther, vol. 4, pp. 1053-1060 (1997).
Mecchia et al., "Type I consensus interferon (CIFN) gene transfer into human melanoma cells up-regulates p53 and enhances cisplatin-induced apoptosis: implications for new therapeutic strategies with IFN-alpha", Gene Ther, vol. 7, pp. 167-179 (2000).
Coleman et al., "Nonviral interferon α gene therapy inhibits growth of established tumors by eliciting a systemic immune response", Hum Gene Ther, vol. 9, pp. 2223-2230 (1998).
Horton et al., "A gene therapy for cancer using intramuscular injection of plasmid DNA encoding interferon α", Proc Natl Acad Sci USA, vol. 96, pp. 1553-1558 (1999).

(Continued)

*Primary Examiner*—Q. Janice Li
(74) *Attorney, Agent, or Firm*—Greenblum & Bernstein, P.L.C.

(57) ABSTRACT

Methods of suppressing growth of pancreatic tumors or cancer cells having a K-ras gene point mutation in a mammal, comprising: administering therapeutically effective amounts of adenoviral vector and antisense K-ras expressing vector to pancreatic cancer cells via intratumoral administration, wherein the adenoviral vector comprises a DNA sequence encoding a human IFN-alpha and operably linked to a promoter, and the pancreatic cancer cells to which the adenoviral vector is administered express the human IFN-alpha; and the antisense K-ras expressing vector comprises an antisense K-ras nucleotide sequence, wherein the antisense K-ras nucleotide sequence is operably linked to a promoter, and the pancreatic cancer cells to which the anti-sense K-ras expressing vector is administered express the antisense K-ras nucleotide sequence; whereby expression of the human IFN-alpha and the antisense K-ras nucleotide sequence suppress growth of pancreatic tumor or cancer cells in the mammal.

11 Claims, 13 Drawing Sheets

OTHER PUBLICATIONS

Aoki et al., "Liposome-mediated in vivo gene transfer of antisense K-ras construct inhibits pancreatic tumor dissemination in the murine peritoneal cavity", Cancer Res, vol. 55, pp. 3810-3816 (1995).

Aoki et al., "Suppression of Ki-ras p21 levels leading to growth inhibition of pancreatic cancer cell lines with Ki-ras mutation but not those without Ki-ras mutation", Mol Carcinog, vol. 20, pp. 251-258 (1997).

Ohnami et al., "Identification of genes showing differential expression in antisense K-ras-transduced pancreatic cancer cells with suppressed tumorigenicity", Cancer Res, vol. 59, pp. 5565-5571 (1999).

Rebouillat et al., "The human 2',5'-oligoadenylate synthetase family: interferon-induced proteins with unique enzymatic properties", J Interferon Cytokine Res, vol. 19, pp. 295-308 (1999).

Castelli et al., "A study of the interferon antiviral mechanism: apoptosis activation by the 2-5A system", J Exp Med, vol. 186, pp. 967-972 (1997).

Diaz-Guerra et al., "Activation of the IFN-inducible enzyme RNase L causes apoptosis of animal cells", Virology, vol. 236, pp. 354-363 (1997).

Zhou et al., "Interferon action and apoptosis are defective in mice devoid of 2',5'-oligoadenylate-dependent RNase L", The EMBO Journal, vol. 16, pp. 6355-6363 (1997).

Ohnami et al., "Expression profiles of pancreatic cancer cell lines infected with antisense K-ras-expressing adenoviral vector", Biochemical and Biophysical Research Communication, vol. 309, pp. 798-803 (2003).

Silverman et al., "Control of the ppp(A2'p)$_n$A system in Hela cells: effects of interferon and virus infection", Eur J Biochem, vol. 124, pp. 131-138 (1982).

Buechner et al., "Regression of basal cell carcinoma by intralesional interferon-alpha treatment is mediated by CD95 (Apo-1/Fas)-CD95 ligand-induced suicide", J Clin Invest, vol. 100, pp. 2691-2696 (1997).

Lewis et al., "Inhibition of mitochondrial function by interferon", J Biol Chem, vol. 271, pp. 13184-13190 (1996).

Le Roy et al., "The 2-5A/RNase L/RNase L inhibitor (RLI) pathway regulates mitochondrial mRNAs stability in interferon alpha-treated H9 cells", Journal of Biological Chemistry, vol. 276, pp. 48473-48482 (2001).

Suzuki et al., "Adenovirus-mediated gene transfer of interferon-a improves dimethylnitrosamine-induced liver cirrhosis in rat model", Gene Therapy, vol. 10, pp. 765-773 (2003).

Nakano et al., "Suppression of colorectal cancer growth using an adenovirus vector expressing an antisense K-ras RNA", Molecular Therapy, vol. 3, pp. 491-499 (2001).

Krasnykh et al., "Targeted adenoviral vectors I: transductional targeting", In: Curiel DT, Douglas JT, editors. Adenoviral vectors for gene therapy. San Diego: Academic Press; p. 205-245 (2002).

Martell et al., "Optimizing aptamer activity for gene therapy applications using expression cassette SELEX", Molecular Therapy, vol. 6, 30-36 pp. (2002).

Yamada et al., "Establishment of a human pancreatic adenocarcinoma cell line (PSN-1) with amplifications of both *c-myc* and activated c-Ki-*ras* by a point mutation", Biochemical and Biophysical Research Communications, vol. 140, pp. 167-173 (1986).

Aoki et al., "Efficient generation of recombinant adenoviral vectors by Cre-lox recombination in vitro", Molecular Medicine, vol. 5, pp. 224-231 (1999).

Player et al., "Ribonuclease L, a 2-5A-dependent enzyme: purification to homogeneity and assays for 2-5A binding and catalytic activity", Methods, vol. 15, pp. 243-253 (1998).

Yoshida et al., "Development of gene therapy to target pancreatic cancer", Cancer Science, vol. 95, pp. 283-289 (2004).

Miura et al., "Synergistic cytotoxic effect of antisense K-ras RNA and interferon alpha against pancreatic cancer cells", Molecular Therapy, vol. 7, p. S417, Poster Abstract #1080, published May 1, 2003, accompanied by 12 pages of documents utilized with the subsequent poster session of the American Society of Gene Therapy made by MIURA et al.

\* cited by examiner

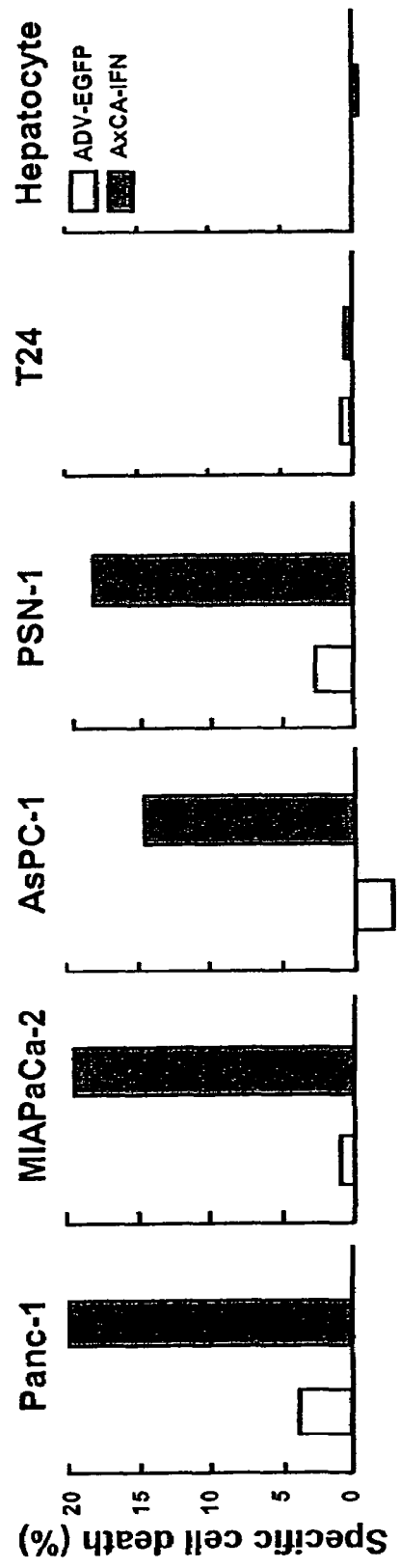
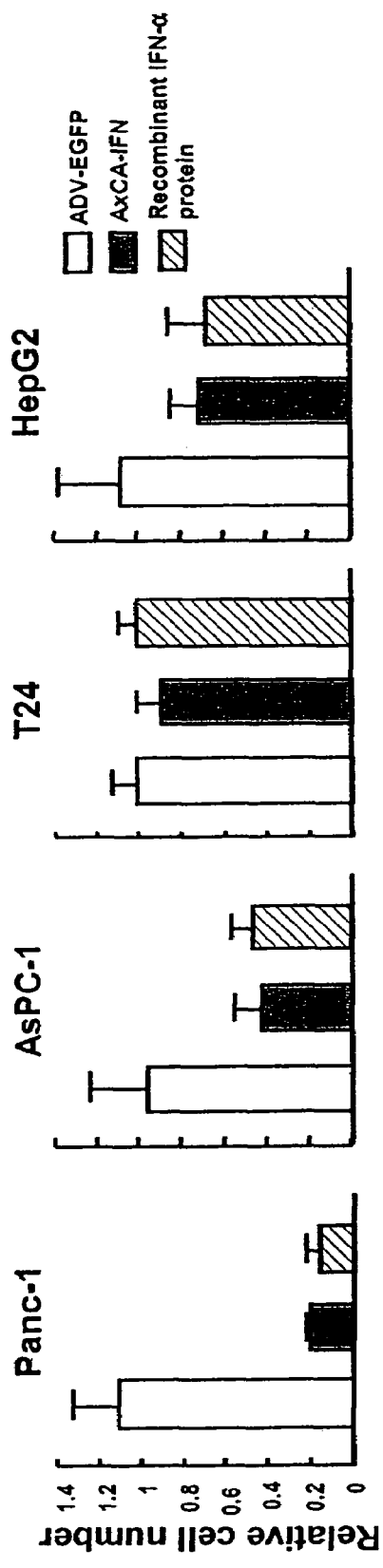
Fig. 3b
Fig. 3c

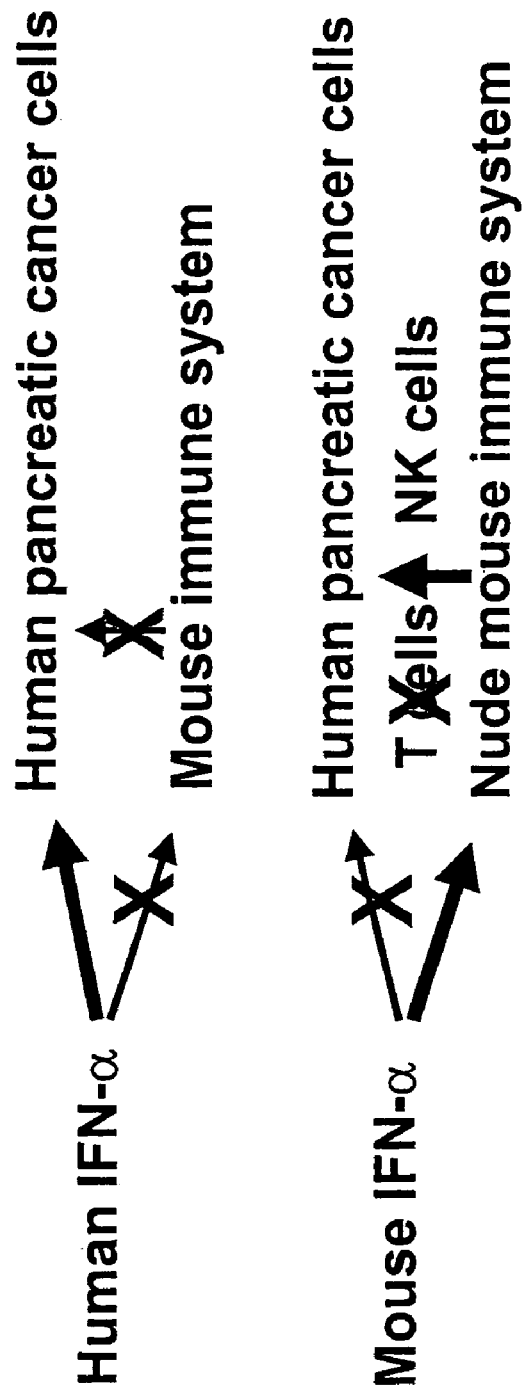
Fig. 7 Study of Antitumor Effect with IFN-α in Immune System

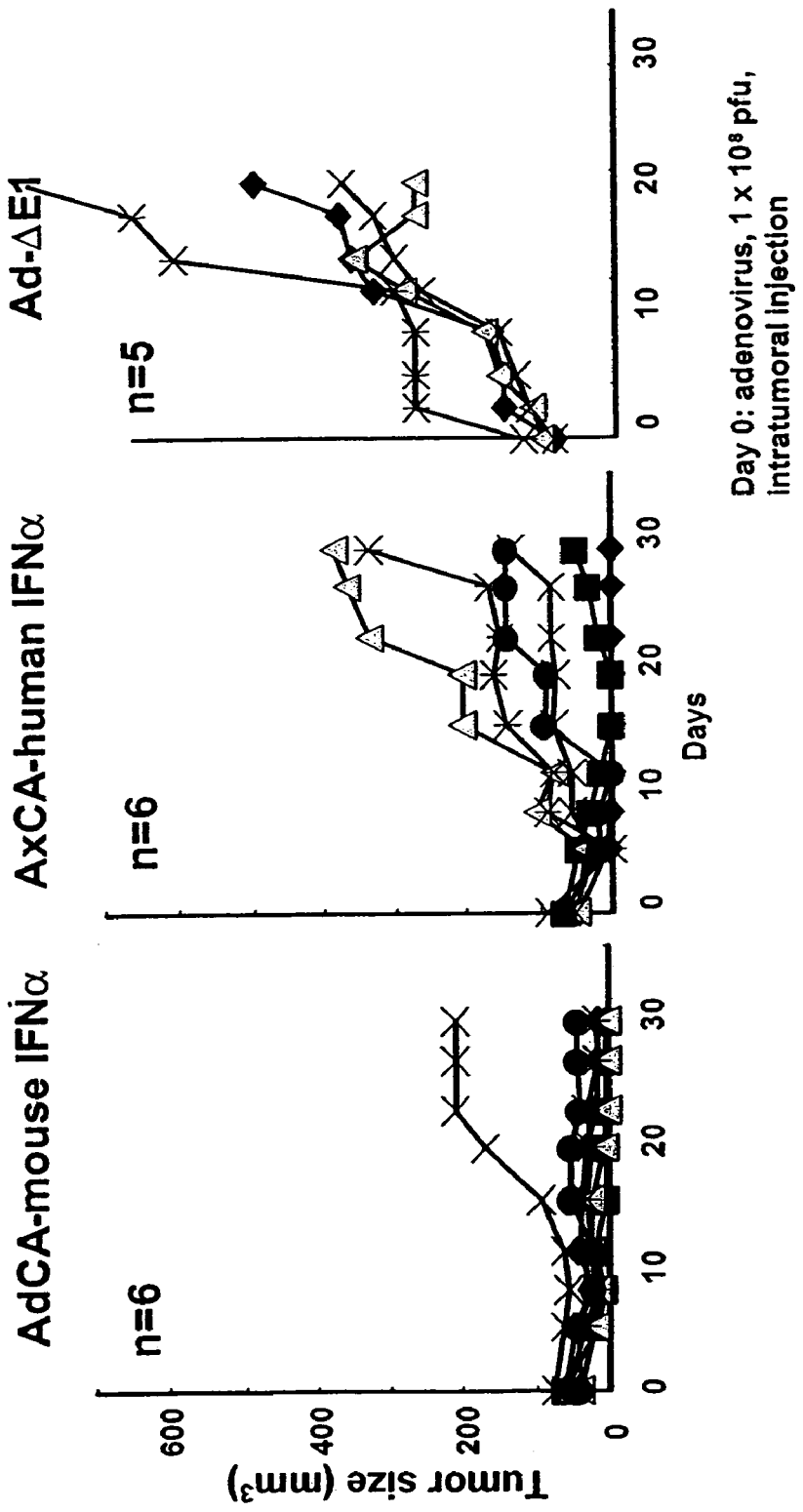
Fig. 8 Antitumor Effect of mouse IFN-α against AsPC-1 Subcutaneous Tumor in Nude Mice

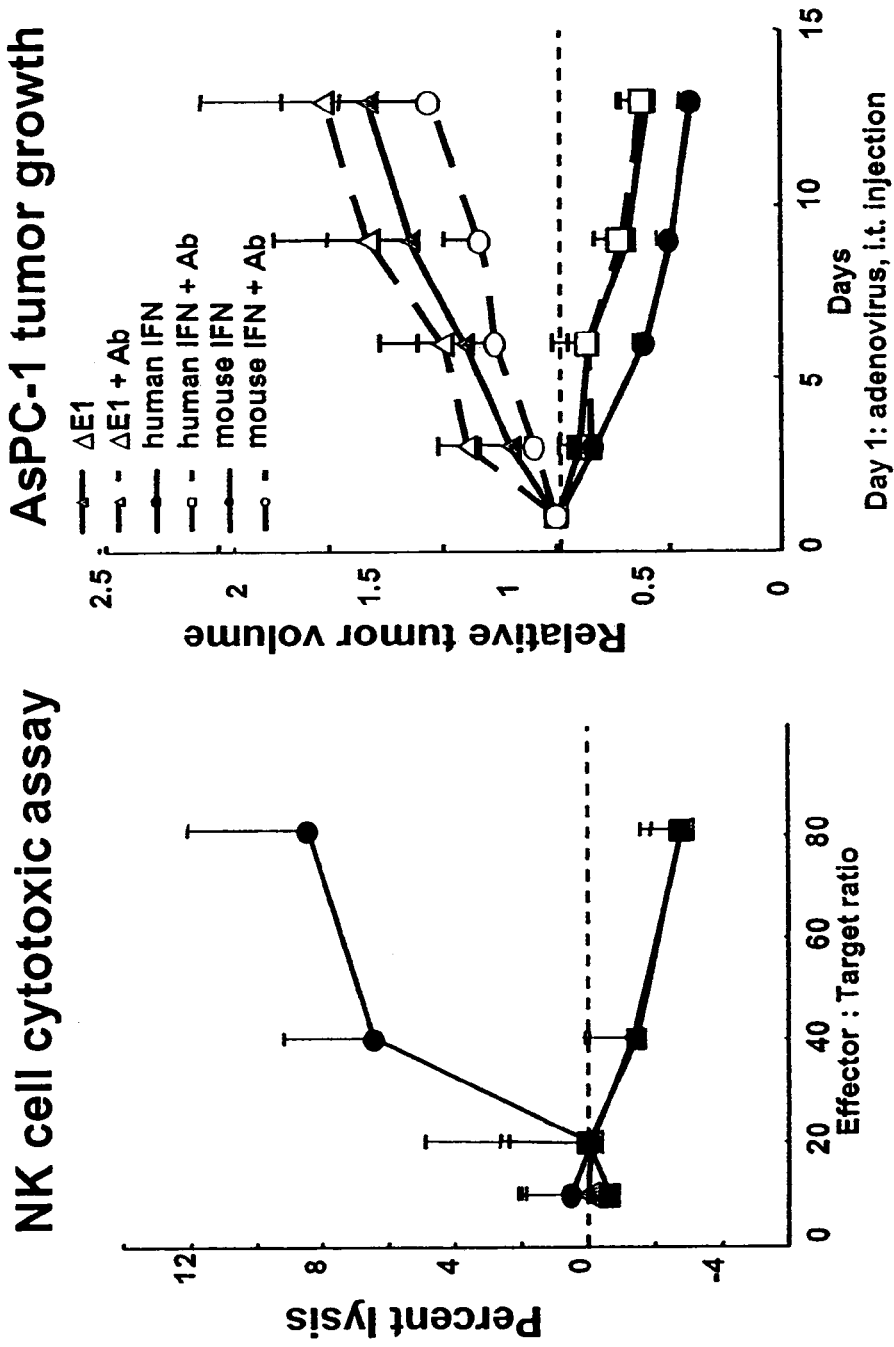
Fig. 9 Inhibitory Effect on Anti-tumor Activity of Mouse IFN-α by NK Cell Depletion

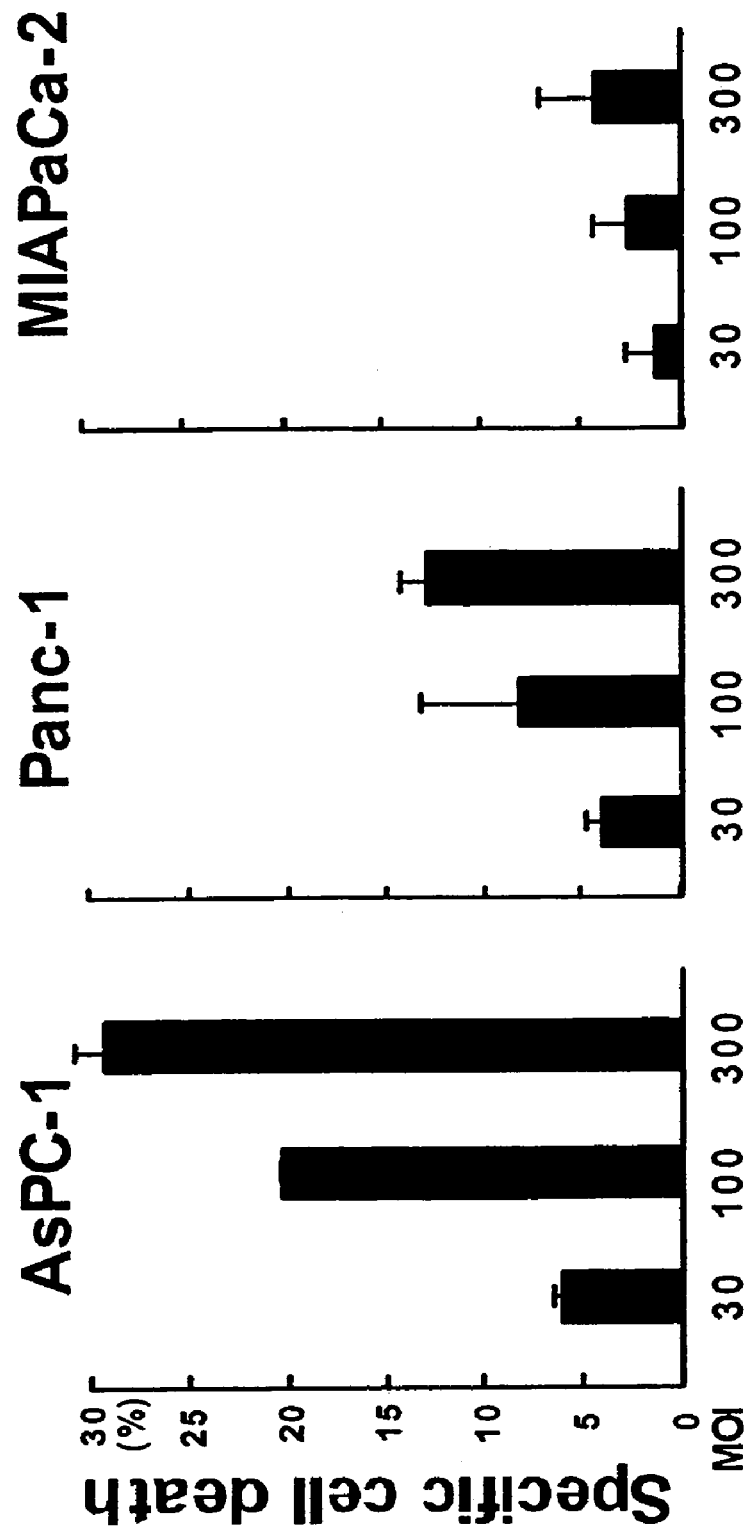
Fig. 10 Apoptotic Cell Death in AxCA-AS-infected Pancreatic Cancer Cells

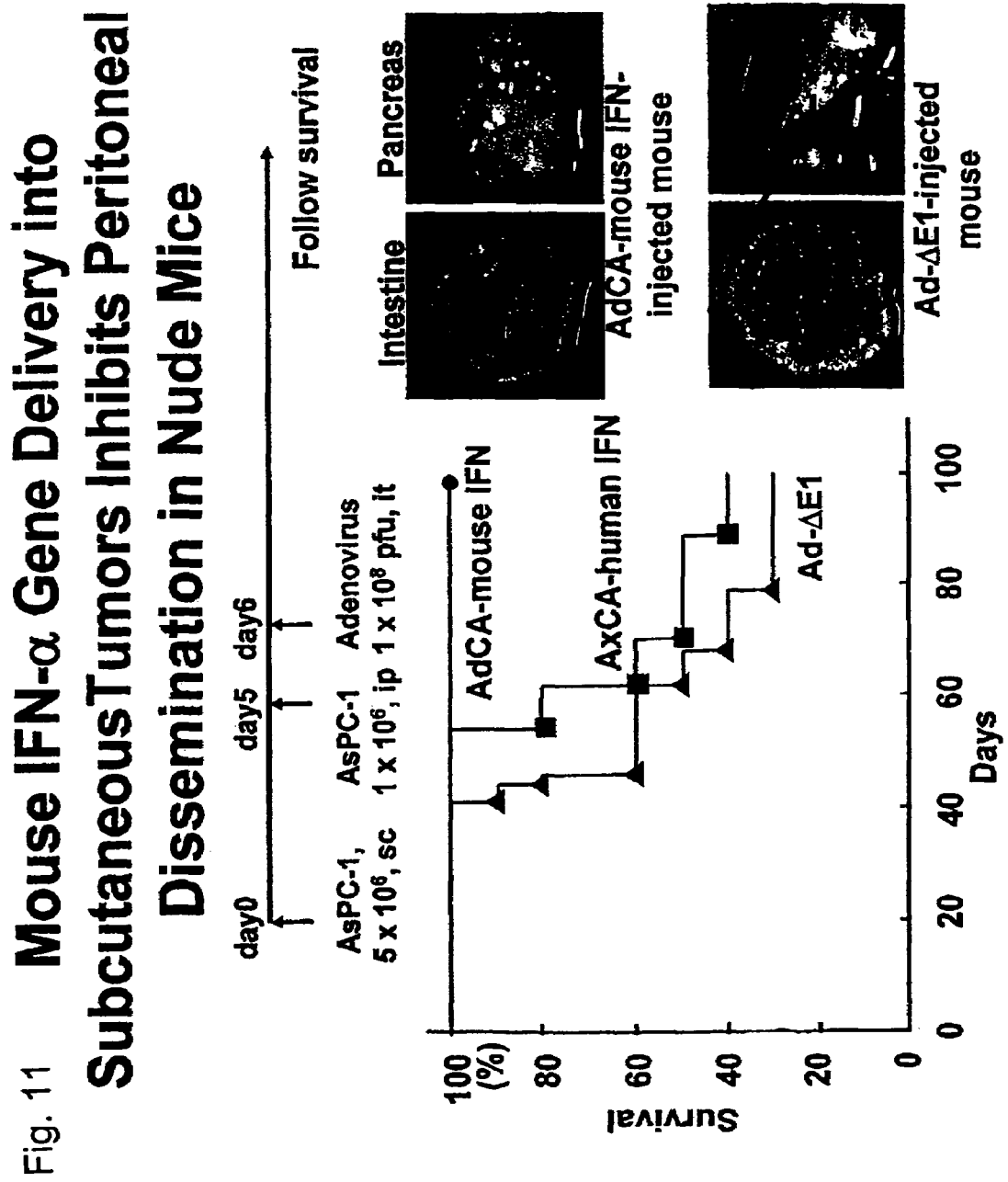
Fig. 11 Mouse IFN-α Gene Delivery into Subcutaneous Tumors Inhibits Peritoneal Dissemination in Nude Mice

INTERFERON ALPHA AND ANTISENSE K-RAS RNA COMBINATION GENE THERAPY

CROSS-REFERENCE TO RELATED APPLICATIONS

This non-provisional U.S. patent application claims benefit of priority of U.S. provisional application No. 60/565,526, filed Apr. 27, 2004, which is incorporated by reference herein in its entirety.

BACKGROUND OF THE INVENTION

1. Field of the Invention

The invention relates to a combination therapy comprising the use of interferon alpha (IFN-α) and antisense K-ras RNA against cancer. The invention also relates to vector-mediated co-expression of antisense K-ras RNA and IFN-α gene for the treatment of cancer. In addition, the invention relates to a synergistic cytotoxic effect of the combination therapy of antisense K-ras RNA and IFN-α against pancreatic cancer.

2. Discussion of Background Information

Adenocarcinoma of the pancreas is highly aggressive and is one of the most difficult cancers to treat at present (1, 2). One major reason for the poor prognosis is that the cancer has a high potential to infiltrate to the surrounding tissues and metastasize even in the early stage. Despite advances in chemo- and radiotherapies and surgical techniques, patients with pancreatic cancer often succumb to local recurrence or metastatic spread (1-3), and new therapeutic strategies against this cancer are an urgent need.

Interferon alpha (IFN-α) protein is a cytokine with multiple biological activities that include antiviral activity, regulation of cell proliferation and differentiation and immunomodulation (4), and it is used worldwide for the treatment of more than 14 types of cancers including some hematological malignancies (hairy cell leukemia, chronic myeloid leukemia, some B- and T-cell lymphoma) and certain solid tumors such as melanoma, renal carcinoma, and Kaposi's sarcoma (4, 5). The growth inhibitory effect of IFN-α protein has been documented in pancreatic cancer cells (6, 7). Recent clinical trials using this cytokine in combination with standard chemotherapeutic drugs also showed some potential anti-tumor activity against pancreatic cancer, but the current clinical protocols failed to document sufficient evidence to enlist pancreatic cancer as a clinically effective target of IFN-α (8-11).

An improved therapeutic effect and safety are possibly achieved by IFN-α in a gene therapy context, because it may allow increased and sustained local concentrations of this cytokine in the target sites while preventing unnecessary systemic distribution (12). Actually, in recent years, IFN-α delivered by adenovirus (12-15), retrovirus (16, 17) or nonviral vectors (18, 19), has been shown to suppress growth of various cancers such as breast cancer, renal cell cancer, basal cell cancer and leukemia in mice. However, the study of IFN-α gene transfer against pancreatic cancer has not been reported. Thus, the antiproliferative effect of IFN-alpha gene transduction into pancreatic cancer cells has been investigated. IFN-alpha expression significantly suppressed cell growth and induced cell death in pancreatic cancer.

It has previously been reported that the expression of antisense K-ras RNA suppressed the growth of pancreatic cells with K-ras point mutation (20-22). The interferon-inducible 2',5'-oligoadenylate synthetase (2-5AS)/RNase L pathway has been shown to activate the apoptotic pathway (23-26). 2-5AS is a double-stranded-RNA-dependent synthetase that generates the activators for Rnase L (23-26) (FIG. 1). The use of IFN-α in combination with antisense K-ras RNA for suppressing growth or inducing apoptosis of pancreatic cancer cells has not been previously reported.

SUMMARY OF THE INVENTION

The invention relates to a method of treating pancreatic cancer. The invention also relates to combination therapy for treating pancreatic cancer comprising administering therapeutically effective amounts of IFN and antisense K-ras to a mammal in need thereof.

The invention provides a method of treating pancreatic cancer cells in a mammal, comprising:

administering therapeutically effective amounts of AxCA-IFN adenoviral vector and antisense K-ras expressing vector to pancreatic cancer cells, wherein the AxCA-IFN adenoviral vector comprises a DNA sequence encoding a human IFN-alpha gene, wherein the human IFN-alpha gene is operably linked to a promoter, and the administered cancer cells express the human IFN-alpha gene; and the antisense K-ras expressing vector comprises a DNA sequence encoding an antisense K-ras gene, wherein the antisense K-ras gene is operably linked to a promoter, and the administered cancer cells express the antisense K-ras gene; and obtaining regression of pancreatic cancer cells in the mammal by expression of the human IFN-alpha gene and the antisense K-ras gene.

The invention may further provide the above method wherein the promoter of the AxCA-IFN adenoviral vector is CAG promoter, wherein the CAG promoter is a beta-actin promoter fused to a cytomegalovirus enhancer element.

The invention may also provide that the promoter of the antisense K-ras expressing vector may be a CAG promoter, wherein the CAG promoter is a beta-actin promoter fused to a cytomegalovirus enhancer element.

The invention may also comprise AxCA-IFN adenoviral vector administered in a dose, for example, ranging from about $4 \times 10^9$ to $20 \times 10^9$ pfu (plaque forming unit)/day/kg body weight.

The invention may also comprise antisense K-ras expressing vector administered in a dose, for example, ranging from about $4 \times 10^9$ to $20 \times 10^9$ pfu (plaque forming unit)/day/kg body weight.

The invention may include administering both vectors to pancreatic cancer cells at the pancreas, administering both vectors to pancreatic cancer cells anywhere in the mammal, or a combination thereof.

The invention may comprise administering both vectors to pancreatic cancer cells at the pancreas, and causing regression of pancreatic cancer cells at the pancreas or regression of pancreatic cancer cells anywhere in the mammal.

The invention may encompass administering both vectors to pancreatic cancer cells at the pancreas, and causing regression of pancreatic cancer cells not localized at the pancreas.

Similarly, the invention relates to administering both vectors to pancreatic cancer cells localized distant from the pancreas, and causing regression of pancreatic cancer cells at the pancreas or pancreatic cancer cells anywhere in the mammal.

Further, the invention may include vectors administered to an identifiable mass of pancreatic cancer cells not localized at the pancreas.

The invention may be to cause a systemic antitumor effect.

The invention provides a combination comprising interferon-alpha expressing vector and antisense K-ras expressing vector.

The invention may provide a method of inducing apoptosis in pancreatic cancer cells in a mammal comprising administering at least one combination using two or more components with at least one component being a vector comprising a DNA sequence encoding interferon-alpha gene and at least one component being a vector comprising a DNA sequence encoding antisense k-ras RNA gene.

The invention also provides a method of treating pancreatic cancer cells in a mammal, comprising: administering a therapeutically effective amount of AxCA-IFN adenoviral vector to pancreatic cancer cells, wherein the AxCA-IFN adenoviral vector comprises a DNA sequence encoding a human IFN-alpha gene, wherein the human IFN-alpha gene is operably linked to a promoter, and the administered cancer cells express said human IFN-alpha gene; and obtaining regression of pancreatic cancer cells in the mammal by expression of the human IFN-alpha gene.

The invention also provides a method of treating pancreatic cancer cells in a mammal, comprising administering therapeutically effective amounts of AxCA-IFN adenoviral vector to pancreatic cancer cells, wherein the AxCA-IFN adenoviral vector comprises a DNA sequence encoding a human IFN-alpha gene, wherein the human IFN-alpha gene is operably linked to a promoter, and the administered cancer cells express said human IFN-alpha gene; activating direct cytotoxicity, indirect immunological antitumor activity, or a combination thereof. The invention also provides a method wherein the indirect immunological antitumor activity may comprise activation of natural killer cells.

The invention also provides a method of treating pancreatic cancer cells in a mammal, comprising inducing indirect immunological antitumor activity that provides systemic immunity against pancreatic cancer.

BRIEF DESCRIPTION OF THE DRAWINGS

The present invention is further described in the detailed description which follows, in reference to the noted plurality of figures by way of non-limiting examples of exemplary embodiments of the present invention, and wherein:

FIGS. 3a, 3b and 3c. Cytotoxic effect of IFN-α gene transfer into cancer and normal cells. Cells were infected with AxCA-IFN or control vector. a) The growth suppression, IFN-α concentration and 2-5AS induction of AxCA-IFN-infected cells. The cells were infected with viruses, and 5-7 days later the cell number was determined by cell proliferative assay. The culture media were harvested 3 days after the adenoviral infection. IFN-α was measured by enzyme-linked immunosorbant assay (Immunotech)(n=3), and the 2-5 AS expression was determined by a radioimmunoassay (Eiken, Tokyo, Japan)(n=3). b) Apoptotic cell death in AxCA-IFN-infected cells. Cells were infected with AxCA-IFN or ADV-AP at moi of 30 (PSN-1 and T24: moi of 100), and apoptotic cells were analyzed by the annexin-V assay 3 days after the infection. The data were expressed as the specific cell death (%) (cell death fraction induced by virus infection (%)–that by mock infection (%)). Results are representative of at least three independent experiments. c) Comparison of growth suppression between the AxCA-IFN-infected cells and the recombinant IFN-α protein-treated cells. The cells were either infected with AxCA-IFN or ADV-EGFP at moi of 30 or treated with the recombinant IFN-α protein added into the culture media once a day for 4 days at concentrations corresponding to those achieved by AxCA-IFN infection at moi of 30 (Table 1). Five days later, cell growth was determined by cell proliferation assay. The assays were repeated a minimum of two times. The data were expressed as the relative cell number ($OD_{450}$ of virus-infected cells or IFN-α protein-treated cells/that of mock-infected cells).

FIG. 7. Study of Antitumor Effect with IFN-alpha in Immune System. We can dissect and examine the two antitumor mechanisms of IFN-alpha gene transfer, taking advantage of the fact that it did not show any cross-species activity in its in vivo effect. When a human IFN-alpha adenovirus is injected into subcutaneous xenografts of human pancreatic cancer cells in nude mice, we can examine a direct antitumor activity of IFN-alpha that is due to the cell death induction in the tumor. When a mouse IFN-alpha is injected into the same subcutaneous tumor system, we can examine an effect that is dependent on the indirect antitumor activity, notably a stimulation of natural killer cells.

FIG. 8. Antitumor Effect of mouse IFN-alpha against AsPC-1 Subcutaneous Tumor in Nude Mice. We examined whether mouse IFN-alpha gene therapy leads to regression of the human AsPC-1 xenograft tumors in nude mice. We injected subcutaneous AsPC-1 tumors with AdCA-mIFN, AxCA-IFN or AdCA-AP at a dose of $1.0\times10^8$ pfu. Although AxCA-IFN effectively suppressed tumor growth, complete tumor regression was observed in only one of 6 mice, and in the particular experiment described here, one of the 6 mice failed to respond to AxCA-IFN (middle panel). AdCA-mIFN caused complete regression in 4 of the 6 mice, and the remaining 2 showed a significant growth retardation (left panel). Tumor size in each mouse (AdCA-mIFN: n=6, AxCA-IFN: n=6, AdCA-AP: n=4) was plotted on the days indicated.

FIG. 9. Inhibitory Effect of Anti-tumor Activity of Mouse IFN-alpha by NK Cell Depletion. To confirm that mouse IFN-alpha gene delivery enhanced NK cell activity, we collected splenocytes from the mice that received intratumoral AdCA-mIFN injection and examined the NK cell function. Increased NK cytolysis was observed in these mice compared with the AxCA-IFN- or AxCA-AP-injected mice (left panel). Pretreatment with an anti-asialo GM1 antibody to purge NK cells reduced the antitumor effect of AdCA-mIFN (right panel) significantly, suggesting that mouse IFN-alpha expression induced the activation of NK cells, which play a major role in the antitumor effect of AdCA-mIFN.

FIG. 10. An Annexin-V assay showing that the infection of AxCA-AS induced cell death in pancreatic cancer cells with K-ras mutation in a dose-dependent manner. Pancreatic cancer cells (AsPC-1, MIAPaCa-2 and Panc-1) were infected with AxCA-AS or control vector AdCA-AP in a 60-mm dish at moi of 10, 30 and 100, and 3 days after infection, apoptotic cells were analyzed by Annexin-V assay (Medical & Biological Laboratories Co. LTD., Nagoya, Japan), which detects phosphatidylserine of inverted plasma membranes. The cells were examined by FACS. An Annexin-V assay showed that the infection of AxCA-AS induced cell death in pancreatic cancer cells with K-ras mutation in a dose-dependent manner. The data were expressed as specific cell death (%) (cell death fraction induced by AxCA-AS (%)–that by AdCA-AP(%)).

FIG. 11. Suppression of tumors at distant sites by the intratumoral injection of AdCA-mIFN into subcutaneous xenografts. Suppression of peritoneal dissemination. When the AsPC-1 subcutaneous tumor was established on the left leg, $1\times10^6$ (left panel) of AsPC-1 cell suspensions were injected into the peritoneal cavity, and 1 day later, $1.0\times10^8$ pfu of viral solution was injected once into the subcutaneous tumor. (Left panel) AdCA-mIFN: n=10, AxCA-IFN: n=10, AdCA-AP: n=10.

DETAILED DESCRIPTION OF THE PRESENT INVENTION

Figure 1:
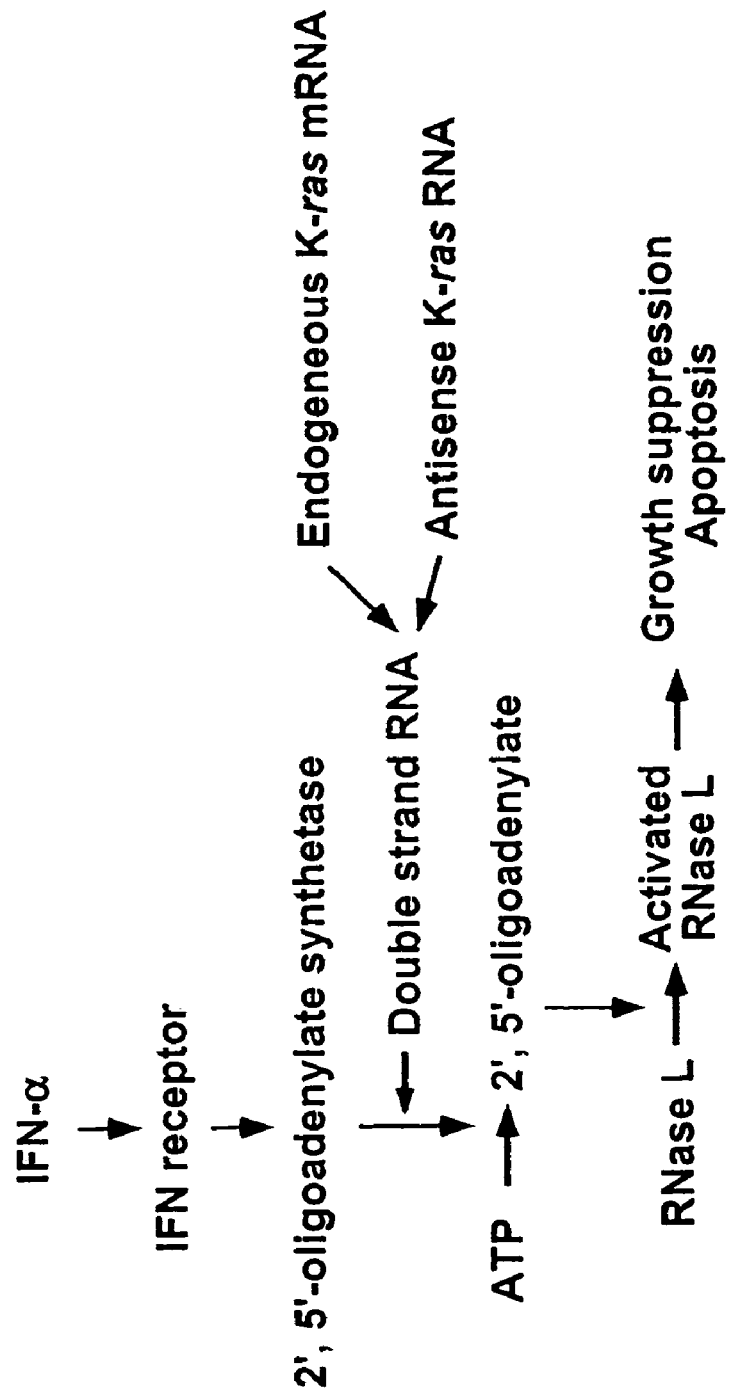
FIG. 1. The role of antisense K-ras RNA in enhancing apoptosis induction by IFN-α. IFN regulates the 2',5'-oligoadenylate synthetase (2-5AS)/RNase L pathway, which induces apoptosis of cells. 2-5AS is activated with double strand RNA. The double strand RNA formed by the binding of antisense and endogenous K-ras RNA may enhance the activation of the 2-5AS/RNase L pathway in the cells.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the figures making apparent to those skilled in the art how the several forms of the present invention may be embodied in practice.

The invention relates to a method of treating pancreatic cancer. The invention relates to therapy for treating pancreatic cancer comprising administering a therapeutically effective amount of IFN-alpha to a mammal in need thereof. The invention also relates to combination therapy for treating pancreatic cancer comprising administering therapeutically effective amounts of IFN-alpha and antisense K-ras to a mammal in need thereof. The invention relates to a method of providing a synergistic anti-cancer combination of IFN-alpha and antisense K-ras to a mammal in need thereof.

The invention generally relates to an antiproliferative effect of IFN-α gene transduction into pancreatic cancer cells. The invention relates to expression of IFN-α to effectively induce growth suppression and cell death in pancreatic cancer cells, an effect which appeared to be more prominent when compared with other types of cancers and normal cells. Another aspect of the invention relates to targeting the characteristic genetic aberration, K-ras point mutation, in pancreatic cancer, and that the expression of antisense K-ras RNA significantly suppresses the growth of pancreatic cancer cells. When these two gene therapy strategies are combined, the expression of antisense K-ras RNA significantly enhanced IFN-α-induced cell death (1.3-3.5 fold), and suppressed subcutaneous growth of pancreatic cancer cells in mice. The invention also relates to a method of suppressing pancreatic cancer cells using double strand RNA formed by antisense and endogenous K-ras RNA in combination with the antitumor activity of IFN-α. The invention relates to the combination of IFN-α and antisense K-ras RNA as an effective gene therapy strategy against pancreatic cancer. The invention also relates to a method of treating pancreatic cancer cells disseminated throughout the body by administering the inventive combination to localized pancreatic cancer cell tumor. The invention also relates to inducing indirect immunological antitumor activity to provide systemic immunity against pancreatic cancer cells.

The invention relates to gene transfer of IFN-α to effectively inhibit cell growth and induce cell death in pancreatic cancer cells. The IFN-α gene transfer-mediated growth-suppressive effect appeared less common and less prominent in other non-pancreatic cancer cells and normal cells. Buechner et al. demonstrated that IFN-α induced the CD95, which interacts with the already expressed CD95L on the cell surface of basal cell carcinoma (29). Evidence is accumulating that the activation of the 2-5AS/RNase L pathway causes apoptosis in tumor cells (30, 31). The present examples showed that IFN-α gene transduction induced the expression of 2-5AS and activation of RNase L in pancreatic cancer cells, and the 2-5AS levels correlate with the growth inhibition. The present examples indicate that IFN-α exerts its antiproliferative effect against pancreatic cancer cells at least in part via the 2-5AS/RNase L pathway.

Figure 4A:
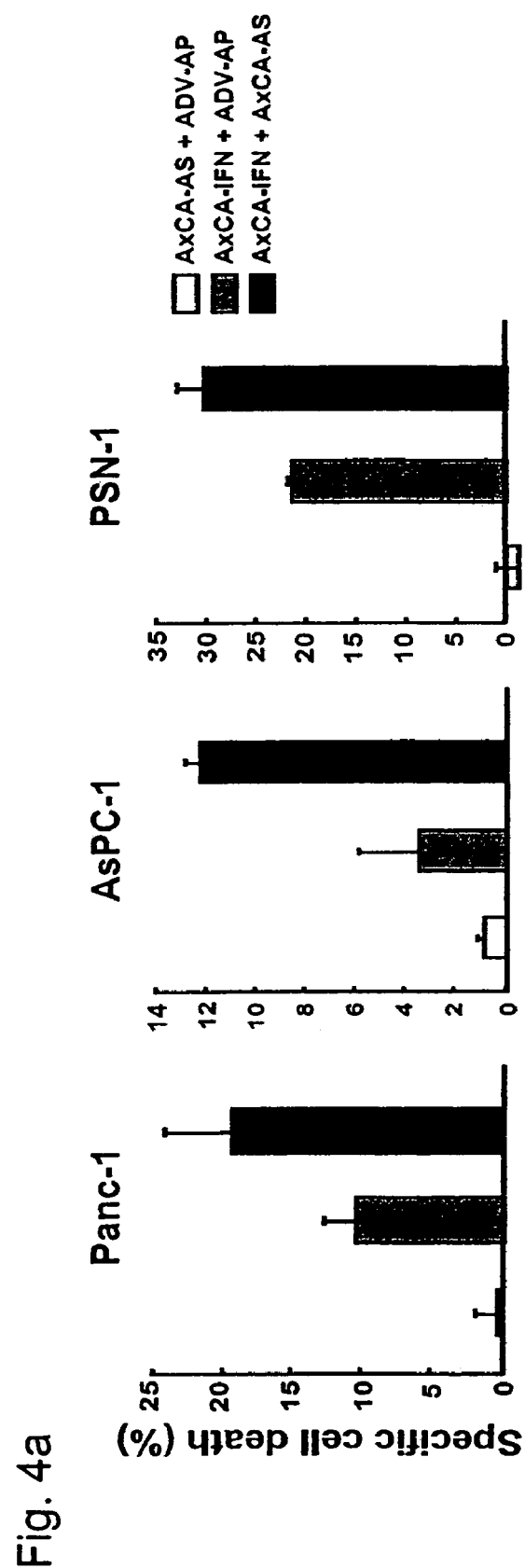
FIGS. 4a and 4b. Combination effect of antisense K-ras RNA and IFN-α. a) Enhancement of IFN-α-induced cell death in pancreatic cancer cells by AxCA-AS. Cells were infected with AxCA-IFN and/or AxCA-AS at moi of 10 (PSN-1: moi of 100) for each vector. To adjust the amount of infected virus in each group, ADV-AP was mixed in AxCA-AS or AxCA-IFN groups. The data was expressed as the specific cell death (%) (cell death fraction induced by AxCA-AS and/or AxCA-IFN (%)–that by ADV-AP (%)). b) The relative cell number of virus-infected cells. The cells were infected with AxCA-IFN and/or AxCA-AS at moi of 1 for Panc-1 and AsPC-1, at moi of 10 for PSN-1 cells, and at moi of 30 for A549, T24 cells and hepatocytes. Cell growth was determined by cell proliferation assay for 6-12 days. Gene transduction efficiency in Panc-1 cells was approximately 20% and IFN-α concentration in the culture medium was 206.5±15.1 IU/ml. The assays were repeated a minimum of two times. The data were expressed as the relative cell number ($OD_{450}$ of AxCA-IFN- and/or AxCA-AS-infected cells/that of ADV-EGFP-infected cells). *; $p<0.01$.

One previous study indicated that the infection of antisense K-ras expressing vector at moi of 10 (or moi of 100 for PSN-1 cells) did not induce a significant cell death in pancreatic cancer cells. (27). Nonetheless, the low-dose AxCA-AS infection in these examples illustrate its enhancing effect on the anti-tumor activity of the similarly low-dose AxCA-IFN infection (FIG. 4a). Because the anti-tumor and apoptosis-inducing effect of the antisense K-ras expressing vector is dose-dependent, the combined anti-tumor effect of the present invention may be further enhanced by increasing the dose of the vector and thus the level of the antisense K-ras RNA expression.

The examples also demonstrated the markedly increased IFN-α concentration in the subcutaneous tumor with little leakage into the serum, indicating the efficacy and safety of the intratumoral injection of the IFN-α adenoviral vector of the present invention. In pancreatic cancer, regional therapy is relevant, because locally advanced cases are surgically unresectable but can be accessible by laparoscopy-mediated injection or ultrasound- or CT-guided percutaneous injection directly to the tumor mass. Although it is often argued that metastasis-prone pancreatic cancer should be regarded as a systemic disease, the survival benefit of the regional control of a locally advanced unresectable pancreatic cancer has been shown in radiotherapy trials (1, 2).

The inventive therapy may be administered by intratumoral administration, such as, for example, by direct injection into the tumor mass. The invention may include injection of a vector directly into a tumor mass. In another embodiment of the invention the inventive therapy may be administered by intra-arterial injection, or as a combination of intratumoral administration and intra-arterial injection. In yet another embodiment of the present invention the intra-arterial route of administration is contemplated for the treatment of advanced or metastatic pancreatic cancer. The present invention may also relate to systemic intravenous injection of an IFN-expressing adenoviral vector to obtain a good confinement of IFN-α expression in the liver while preventing its elevation in the serum. Similar effects were observed in a rat model study (32). In another embodiment of the present invention, since the liver is a frequent metastatic organ of pancreatic cancer, increased concentration of IFN-α in the liver may be a useful strategy for preventing and treating hepatic metastasis of pancreatic cancer optionally in combination with the administration and/or expression of antisense K-ras RNA.

The present invention relates to a method of treating adenocarcinoma of the pancreas, including pancreatic cancer that has infiltrated to the surrounding tissues or is at an early stage of metastasis. The present invention may be practiced in addition to or in place of chemotherapies, radiotherapies, and/or surgical techniques.

Interferon alpha (IFN-α) protein, as used herein, refers to a cytokine with multiple biological activities that include antiviral activity, regulation of cell proliferation and differentiation and immunomodulation, as exemplified in cited document (4), and it is used worldwide for the treatment of more than 14 types of cancers including some hematological malignancies (hairy cell leukemia, chronic myeloid leukemia, some B- and T-cell lymphoma) and certain solid tumors such as melanoma, renal carcinoma, and Kaposi's sarcoma, as exemplified in cited documents (4, 5). The IFN-α protein of the present invention has a growth inhibitory effect in pancreatic cancer cells, as exemplified in cited documents (6, 7). Thus, the IFN-α protein may be used in combination with standard chemotherapeutic drugs for anti-tumor activity against pancreatic cancer, as exemplified in cited documents (8-11).

An improved therapeutic effect and safety may be achieved by IFN-α in a gene therapy context of the present invention, because it may allow increased and sustained local concentrations of this cytokine in the target sites while preventing unnecessary systemic distribution, as exemplified in cited document (12).

The present invention relates to the expression of antisense K-ras RNA causing suppressed growth of pancreatic cells with K-ras point mutation, as exemplified in cited documents (20-22). The interferon-inducible 2',5'-oligoadenylate synthetase (2-5AS)/RNase L pathway has been shown to activate the apoptotic pathway (23-26), and may thus promote the apoptosis of pancreatic cancer cells being treated by a method of the present invention. 2-5AS is a double-stranded-RNA-dependent synthetase that generates the activators for Rnase L (23-26). The double strand RNA formed by the binding of antisense and endogenous K-ras RNA may be one mechanism wherein antisense K-ras enhances the activation of the 2-5AS/RnaseL apoptotic pathway in pancreatic cancer cells being treated by a method of the present invention. The present invention also relates to use of IFN-α in combination with antisense K-ras RNA for suppressing growth or inducing apoptosis of pancreatic cancer cells.

With respect to safety, the very limited antiproliferative effects of IFN-α and antisense K-ras RNA for normal cells such as hepatocytes (FIG. 3a)(33) suggest the biological safety of the present inventive combination therapy. In another embodiment of the present invention, redirection of adenoviral vector tropism to specific cell types, such as, for example, on the basis of the modification of viral capsid proteins, providing one possible means for enhanced therapeutic targeting (34). However, since it is known from clinical experience that IFN protein treatment may cause acute adverse effects, one embodiment of the present invention optionally comprises a safety device for terminating vector-induced IFN-α production if a significant adverse effect appears. For example, one embodiment of the present invention comprises a Cre/IoxP-mediated shut-off system of IFN-α expression in vivo, to optionally limit IFN-α expression or its overexpression, or to avoid IFN-α overdose (32). Other embodiments of the present invention may optionally independently comprise antidote molecules to control the toxicity of cytokine gene therapy, such as, for example, anti IFN antibody, RNA aptamers (35) or RNAi.

The following are non-limiting examples of the present invention.

EXAMPLES

Example 1

Methods

A. Cell Lines and Culture Conditions

Five human pancreatic cancer cell lines (AsPC-1, MIAPaCa-2, Panc-1, PSN-1, 766T), 4 human non-pancreatic cancer cell lines (hepatocellular carcinoma cell line: HepG2, non-small cell lung cancer cell line: A549, prostate cancer cell line: PC-3, bladder cancer cell line: T24) and 3 primary cultures of human normal cell lines (hepatocytes, human umbilical vascular endothelial cells: HUVEC, smooth muscle cells: SMC) were used in this study. All cancer cell lines except for PSN-1 were obtained from American Tissue Culture Collection, and PSN-1 was established in our laboratory (36). All cancer cell lines except for 766T and HepG2 cells were maintained in an RPMI-1640 medium with 10% fetal bovine serum (FBS), and the 766T and HepG2 cells were cultured in Dulbecco's modified eagle's medium with 10% FBS. Primary cultures of normal human cells were purchased from Dainippon Pharmaceutical Co. (Osaka, Japan) and were cultured according to the supplier's instructions. The K-ras gene was sequenced for all of the pancreatic cancer cell lines. Mutations in codon 12 of the K-ras gene were confirmed for the AsPC-1 (GGT to GAT), Panc-1 (GGT to GAT), MIAPaCa-2 (GGT to TGT) and PSN-1 (GGT to CGT) cell lines, whereas the 766T cell line had a mutation (CM to CAC) in codon 61 of the K-ras gene.

B. Construction of Recombinant Adenovirus Vectors

The recombinant adenovirus vectors expressing antisense K-ras RNA (AxCA-AS), interferon-α 2a (AxCA-IFN), enhanced green fluorescein protein (ADV-EGFP), and alkaline phosphatase cDNA (ADV-AP) were prepared as described (32, 33, 37). A cesium chloride-purified virus was desalted using a sterile Bio-Gel P-6 DG chromatography column (Econopac DG 10, BioRad, Hercules, Calif.) and diluted for storage in a 13% glycerol/PBS solution to yield a final concentration of $1 \times 10^{10}$ pfu/ml.

The recombinant adenovirus vectors expressing human interferon-α 2a (AxCA-IFN), mouse interferon-α (AdCA-mIFN), enhanced green fluorescein protein (AdCA-EGFP), and alkaline phosphatase cDNA (AdCA-AP) were prepared as described (Aoki et al, 1999; Nakano et al, 2001; Suzuki et al, 2003). A cesium chloride-purified virus was desalted using a sterile Bio-Gel P-6 DG chromatography column (Econopac DG 10, BioRad, Hercules, Calif.) and diluted for storage in a 13% glycerol/PBS solution.

C. Western Blot Analysis

The cells were lysed in an RIPA buffer (10 mM Tris-HCl, pH 7.4, 1% deoxycholate, 1% Nonidet-40, 150 mM NaCl, 0.1% SDS, 0.2 mM phenylmethylsulfonyl fluoride, 1 µg/ml aprotinin, 1 µg/ml leupeptin, 10% 2-mercaptoethanol). Eighty micrograms of cell lysates were heated at 95° C. for 5 min, size-fractionated by 8-16% SDS-polyacrylamide gel (TEFCO, Tokyo, Japan) and electroblotted onto polyvinylidene difluoride membranes (NEM Life Science Products Inc., Boston, Mass.). The interferon α/β receptors (IFNAR1 and IFNAR2) were detected by specific mouse monoclonal antibodies (Santa Cruz Biotechnology Inc., Santa Cruz, Calif.) using enhanced chemiluminescence system (Amersham Pharmacia Biotech, Piscataway, N.J.).

D. In Vitro Growth Analysis

The cell lines were seeded at $2 \times 10^3$ per well in 96-well plates and infected with AxCA-IFN, AxCA-AS or ADV-EGFP at moi of 10, 30 and 100. PSN-1 was infected with adenoviruses at moi of 100, 300 and 1000, because the cells are relatively resistant to adenoviral infection. The cell numbers were assessed by a calorimetric cell viability assay using a water-soluble tetrazolium salt (Tetracolor One; Seikagaku Corp., Tokyo, Japan) 5-7 days after the infection. The absorbance was determined by spectrophotometry using a wavelength of 450 nm with 595 nm as a reference. The assays (carried out in 8 wells) were repeated a minimum of two times and the mean±standard deviation was plotted. The data were expressed as the percent growth suppression, which was determined by the formula:

$$\{1 - (OD_{450} \text{ of } AxCA\text{-}IFN\text{-infected cells}/OD_{450} \text{ of } ADV\text{-}EGFP\text{-infected cells})\} \times 100$$

The data was also expressed as the relative cell number ($OD_{450}$ of AxCA-IFN or AdCA-mIFN-infected cells/$OD_{450}$ of AdCA-EGFP-infected cells).

E. Ribosomal RNA Cleavage Assay

Panc-1 cells were infected either with AxCA-IFN plus AxCA-AS or AxCA-IFN plus ADV-EGFP in a 15-cm dish at moi of 30, and 4 days later the cell pellets were lysed in approximately 1.5-fold volume of Nonidet P-40 lysis buffer (10 mM Hepes, pH7.5, 90 mM KCl, 1.0 mM magnesium acetate, 0.5% (v/v) Nonidet P-40, 2.0 mM fresh 2-mercaptoethanol, 100 µg/ml fresh leupeptin). The lysates containing 200 µg of protein were incubated with 10× cleavage buffer (100 mM Hepes, pH7.5, 1 M KCl, 50 mM magnesium acetate, 10 mM ATP, 0.14 M 2-mercaptoethanol) and 1 µM of 2-5A activator at 30° C. for 10 min (38). Total RNA was extracted from the cleavage reaction using Isogen RNA isolation reagent (Nippon Gene, Tokyo, Japan). Five micrograms of total RNA were electrophoresed on a 1.8% agarose gel, transferred onto a nylon membrane (Hybond N; Amersham Pharmacia Biotech) and hybridized with a $^{32}$P-labeled cDNA of 18S rRNA in 50% foramide, 5× Denhardt's solution, 0.1% SDS, 5×SSPE, and 100 µg/ml of salmon testis DNA at 42° C. for 16 hr. The membranes were then washed in 0.1×SSC and 0.1% SDS. The autoradiogram was analyzed by a densitometer.

F. Annexin V Assay

Cultured cells were infected with AxCA-IFN, AxCA-AS and/or ADV-AP in a 6-cm dish, and 3 days later prepared by the treatment of 2 mM EDTA and then stained with annexin-V-FITC (Medical & Biological Laboratories Co. LTD., Nagoya, Japan), which detects phosphatidylserine of inverted plasma membranes, and then were examined by FACS analysis. The assays were carried out in triplicate, and the mean±standard deviation was plotted.

G. Terminal Deoxynucleotidyltransferase-mediated dUTP-digoxigenin Nick-end-labeling (TUNEL) Assay Nucleosome-sized DNA fragments of formalin-fixed tissue sections infected with AxCA-IFN or ADV-AP were identified by the TUNEL assay with peroxidase as directed by the manufacturer's instruction (ApopTag in situ apoptosis detection kit; Intergen Company, Purchase, N.Y.), and examined by microscopy.

Example 2

Gene Transduction into Subcutaneous Tumor: I

AsPC-1 cells were used in an in vivo gene transfer model in Five week-old male Balb/c nude mice obtained from Charles River Japan (Kanagawa, Japan), and kept in a specific-pathogen-free environment. AsPC-1 cell suspensions ($5 \times 10^6$ cells per 50 µl) were injected subcutaneously into the left flank, and a total of $5 \times 10^8$ or $1 \times 10^8$ pfu of viral solution was injected once into the tumor with a 27-gauge hypodermic needle, when the tumor mass was established (~0.6 cm in diameter). Control tumor-bearing mice were injected with $5 \times 10^8$ or $1 \times 10^8$ pfu of ADV-AP alone. Three groups of mice were injected with AxCA-AS and ADV-AP, AxCA-IFN and ADV-AP, or AxCA-IFN and AxCA-AS ($2.5 \times 10^8$ or $0.5 \times 10^8$ pfu each), respectively. One mouse from ADV-AP control group and AxCA-IFN/ADV-AP ($5 \times 10^8$ pfu) injected group was sacrificed for a histological examination of the subcutaneous tumor by hematoxylin-eosin staining and TUNEL assay, another 3 mice from each group were sacrificed for the measurement of IFN-α concentration in the subcutaneous tumor and the serum, and the remaining animals were observed for tumor growth. The short (r) and long (l) diameters of the tumors were measured and the tumor volume of each was calculated as $r^2l/2$.

Example 3

Figure 2:
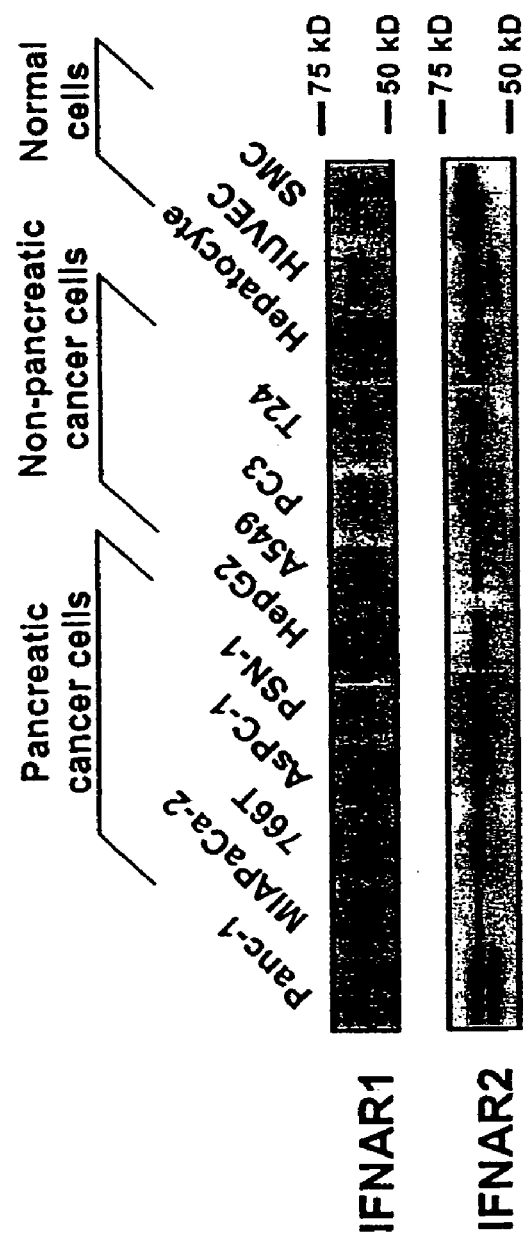
FIG. 2. Western blot analyses of two subunits of interferon α/β receptor. Eighty micrograms of the cell lysates were analyzed.
Figure 3A:
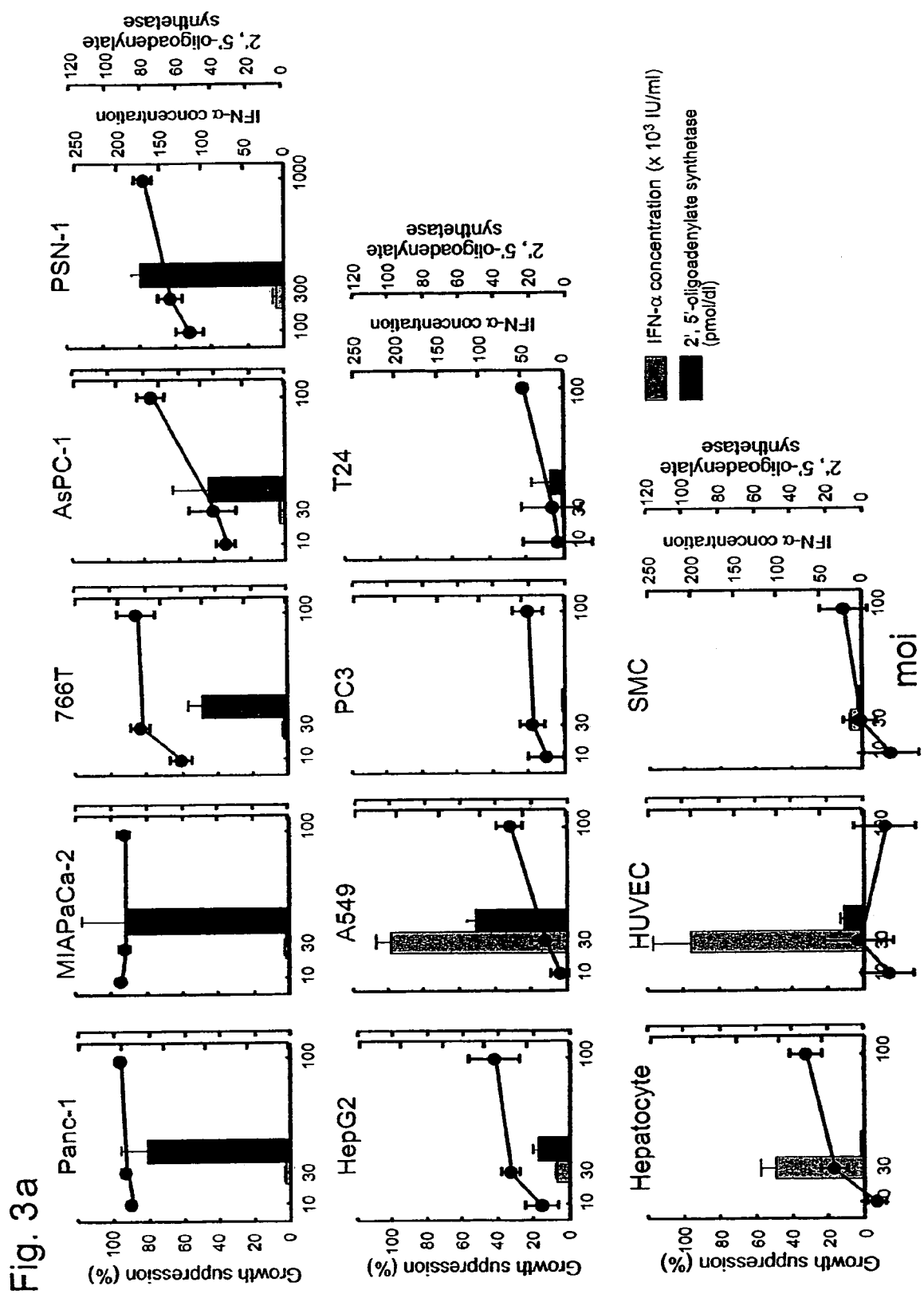

Cytotoxic Effect of Interferon-α Gene Transduction into Pancreatic Cancer Cells To study whether the expression of the human IFN-α gene effectively inhibits cell growth, 5 pancreatic cancer cell lines, 4 non-pancreatic cancer cell lines and 3 primary cultures of human normal cells were infected with the AxCA-IFN adenoviral vector. Western blot analysis showed that all cell lines express two subunits of interferon α/β receptor (IFNAR1 and IFNAR2) in varying degrees (FIG. 2). The amounts of IFN-α secreted from AxCA-IFN-infected cells were dependent on the adenoviral dose but varied substantially among the cell lines (Table 1). The concentrations in the culture medium of infected pancreatic cancer cells were rather lower than those of HepG2, A549, hepatocytes and HUVEC. The infection with AxCA-IFN showed some growth suppression of non-pancreatic cancer cells and hepatocytes, whereas the vector inhibited cell growth and induced cell death in pancreatic cancer cells much more effectively as compared with non-pancreatic cancer and normal cells (FIGS. 3a and b).

The IFN-α-induced apoptosis in the pancreatic cancer cells was confirmed with TUNEL staining. To confirm that the amounts of IFN-α produced by the AxCA-IFN infection were sufficient for the observed antiproliferative effect, a recombinant IFN-α protein was added into the culture medium of the cells at concentrations corresponding to those achieved by the AxCA-IFN infection. The growth suppressions by the exogenously added IFN-α protein were comparable with those observed by the AxCA-IFN infection (FIG. 3c).

The high sensitivity of pancreatic cancer cells to IFN-α was examined in expression of 2-5AS in the cells infected with AxCA-IFN at moi of 30. The 2-5AS was significantly induced in pancreatic cancer cells in response to IFN-α gene transfer in spite of the rather lower concentrations of IFN-α, whereas such induction was weak or not observed for normal cells and non-pancreatic cancer cells except for A549 (FIG. 3a). No cell line infected with AxCA-EGFP at moi of 30 showed detectable levels of 2-5AS.

IFN-alpha gene transfer may activate two antitumor mechanisms. First, a direct antitumor activity of IFN-alpha due to induction of tumor cell death; and second, an IFN-alpha induced indirect antitumor activity, such as, for example, innate antitumor immunity. Also, for example, innate antitumor immunity may result from IFN-alpha induced stimulation of natural killer cells (See FIG. 9). Two antitumor mechanisms of IFN-alpha gene transfer were dissected and examined, taking advantage of the fact that it did not show any cross-species activity in its in vivo effect. (See FIG. 7) When a human IFN-alpha adenovirus was injected into subcutaneous xenografts of human pancreatic cancer cells in nude mice, a direct antitumor activity of IFN-alpha that was due to the cell death induction in the tumor could be examined. When a mouse IFN-alpha was injected into the same subcutaneous tumor system, an effect that was dependent on the indirect antitumor activity, notably a stimulation of natural killer cells could be examined.

FIG. 8 shows the antitumor effect of mouse IFN-alpha against AsPC-1 subcutaneous tumor in nude mice. It was examined whether mouse IFN-alpha gene therapy leads to regression of the human AsPC-1 xenograft tumors in nude mice. Subcutaneous AsPC-1 tumors were injected with AdCA-mIFN, AxCA-IFN or AdCA-AP at a dose of $1.0 \times 10^8$ pfu. Although AxCA-IFN effectively suppressed tumor growth, complete tumor regression was observed in only one of 6 mice, and in the particular experiment described here, one of the 6 mice failed to respond to AxCA-IFN (FIG. 8, middle panel). AdCA-mIFN caused complete regression in 4 of the 6 mice, and the remaining 2 showed a significant growth retardation (FIG. 8, left panel). Tumor size in each mouse (AdCA-mIFN: n=6, AxCA-IFN: n=6, AdCA-AP: n=4) was plotted on the days indicated.

Example 4

Cytotoxic Effect of K-ras Antisense Gene Transduction into Pancreatic Cancer Cells FIG. 10 provides an Annexin-V assay showing that the infection of AxCA-AS induced cell death in pancreatic cancer cells with K-ras mutation in a dose-dependent manner. Pancreatic cancer cells (AsPC-1, MIAPaCa-2 and Panc-1) were infected with AxCA-AS or control vector AdCA-AP in a 60-mm dish at moi of 10, 30 and 100, and 3 days after infection, apoptotic cells were analyzed by Annexin-V assay

TABLE 1

| | | | | IFN-α concentration in the culture medium | | | | |
|---|---|---|---|---|---|---|---|---|
| | mol | Panc-1 | MIAPaCa-2 | 766T | AsPC-1 | PSN-1 | HepG2 | A549 |
| EGFP | 100 | <0.05 | <0.05 | <0.05 | <0.05 | <0.05 | <0.05 | 0.05 ± 001 |
| IFN-α | 10 | 0.8 ± 0.8 | 0.7 ± 0.4 | 0.7 ± 0.5 | 4.2 ± 1.6 | 4.4 ± 1.6 | 13.5 ± 6.2 | 65.4 ± 7.8 |
| | 30 | 6.1 ± 1.5 | 5.4 ± 1.8 | 3.6 ± 2.6 | 6.5 ± 1.3 | 9.4 ± 3.2 | 15.7 ± 2.4 | 210.2 ± 18.8 |
| | 100 | 24.3 ± 6.5 | 12.9 ± 0.8 | 11.9 ± 4.6 | 24.0 ± 1.3 | 17.0 ± 2.7 | 218.9 ± 8.2 | 618.5 ± 54.5 |
| | | | mol | PC-3 | T24 | Hepatocyte | HUVEC | SMC |
| | | EGFP | 100 | <0.05 | <0.05 | <0.05 | <0.05 | <0.05 |
| | | IFN-α | 10 | 1.4 ± 0.4 | 1.4 ± 0.5 | 1.5 ± 1.2 | 24.2 ± 1.7 | 3.7 ± 0.8 |
| | | | 30 | 2.0 ± 0.8 | 3.0 ± 0.4 | 103.0 ± 17.6 | 204.4 ± 45.0 | 12.0 ± 1.6 |
| | | | 100 | 4.1 ± 3.0 | 12.9 ± 1.9 | 132.0 ± 7.5 | 909.1 ± 23.3 | 51.1 ± 16.4 |

($\times 10^3$ IU/ml)
The culture media were harvested 5 days after the adenoviral infection. IFN-α was measured by enzyme-linked immunosorbant assay (Immunotech, Marseille Cedex, France).

(Medical & Biological Laboratories Co. LTD., Nagoya, Japan), which detects phosphatidylserine of inverted plasma membranes. The cells were examined by FACS. An Annexin-V assay showed that the infection of AxCA-AS induced cell death in pancreatic cancer cells with K-ras mutation in a dose-dependent manner. The data were expressed as specific cell death (%) (cell death fraction induced by AxCA-AS (%)–that by AdCA-AP(%)).

Example 5

Combination Effect of Antisense K-ras RNA and IFN-α

Figure 4B:
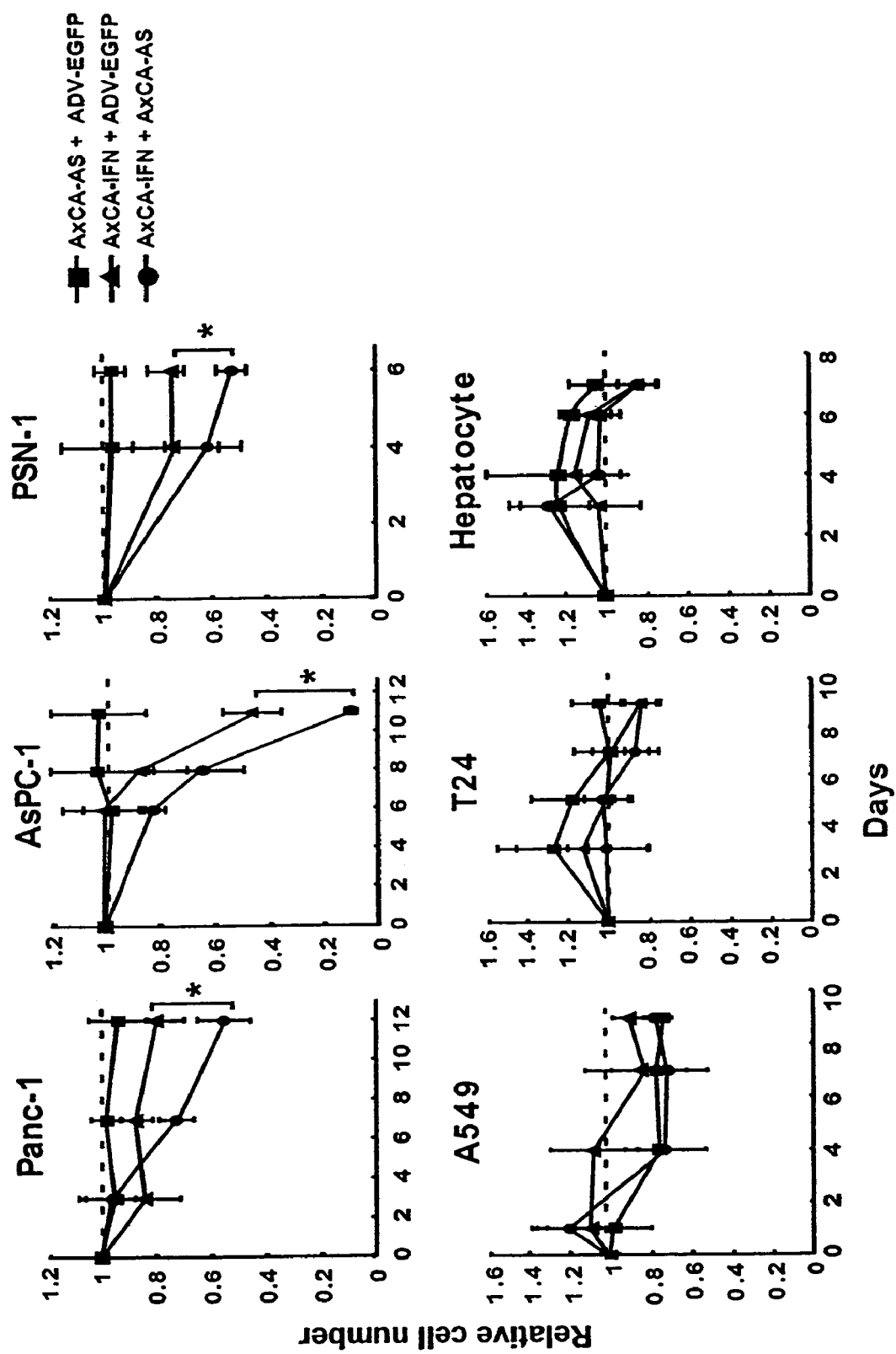

Since it is known that IFN-regulated 2-5AS is activated with double strand RNA and the activation of 2-5AS-dependent RNase L induces apoptosis of cells, enhancement of IFN-α-induced cell death by a low-dose of the antisense K-ras RNA vector (moi of 10 for Panc-1 and AsPC-1, and moi of 100 for PSN-1) was examined. At moi of 30 (or 300 for PSN-1), the antisense K-ras expressing vector effectively caused an 8-30 fold downregulation of K-ras mRNA and resulted in the inhibition of cell growth, and at moi of 100 (or 1000 for PSN-1), the vector significantly induced cell death in pancreatic cancer cells (27). Although the AxCA-AS infection alone at moi of 10 did not induce cell death, its co-infection with AxCA-IFN showed a significant enhancement of cell death (1.3-3.5 fold)(FIG. 4a). Then the combination growth suppressive effects in pancreatic cancer cells (Panc-1, AsPC-1 and PSN-1), non-pancreatic cancer cells (A549 and T24) and primary culture of the hepatocytes was examined. The significant synergistic growth suppression was observed in pancreatic cancer cell lines at moi of 1 (or 10 for PSN-1), whereas other cancer cells and hepatocytes did not show the combination effect even at moi of 30 (FIG. 4b).

Example 6

Enhancement of IFN-α-induced RNase L Activation by Antisense K-ras RNA

Figure 5A:
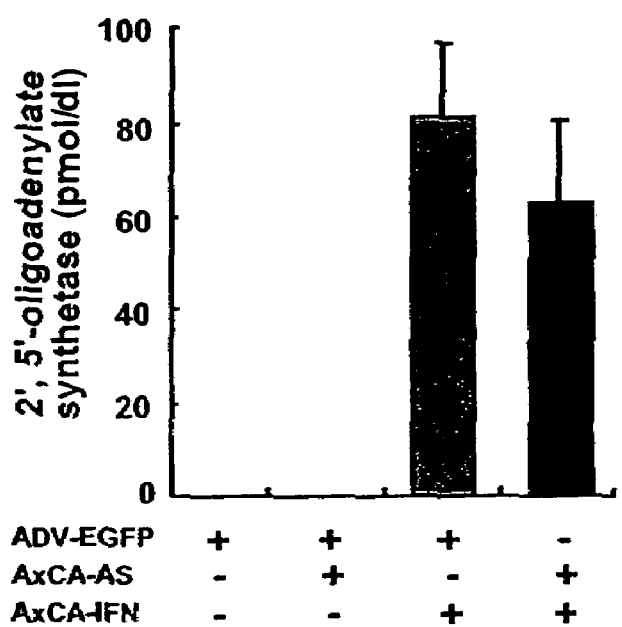
FIGS. 5a and 5b. Enhancement of IFN-α-induced degradation of rRNA by antisense K-ras RNA. Panc-1 cells were infected with AxCA-IFN and/or AxCA-AS each at moi of 30. a) 2-5 AS expression in Panc-1 cells infected with adenoviruses. The assays were carried out in triplicate, and the mean±standard deviation was plotted. b) Degradation of 18S rRNA. Four days after the adenoviral infection, the cell lysates were incubated with 1 μM of 2-5A activator, and Northern blot of the total RNA was hybridized with a cDNA probe for 18S rRNA. The 18S rRNA cleavage product is indicated (arrow).
Figure 5B:

To examine whether the expression of antisense K-ras RNA enhances IFN-α-induced RNase L activation, the cell lysates of the adenovirus-infected Panc-1 cells were incubated with 2-5A activator, and total RNA was analyzed for ribosomal RNA cleavage. Although the expression level of 2-5AS in the cells co-infected with AxCA-IFN and AxCA-AS was equivalent to that in cells infected with AxCA-IFN and ADV-EGFP (FIG. 5a), specific 18S rRNA degradation products, characteristic of 2-5AS-dependent RNase L cleavage (28), were detected only in AxCA-IFN-infected cells and this ribonuclease activity increased by co-infection with AxCA-AS (FIG. 5b). By densitometry analysis, the signal of the cleavage products compared with that of the 18S rRNA was 29.8% in the co-infected lane and 12.0% in the AxCA-IFN-infected lane (FIG. 5b). This synergistic effect was not observed in hepatocytes, which was compatible with the results obtained from the growth inhibition study (FIG. 4b).

Example 7

Anti-Tumor Effect of Combination Therapy in Subcutaneous Tumor Model

To examine the combination effect of AxCA-IFN and AxCA-AS in suppressing tumor growth in vivo, AsPC-1 cells were inoculated subcutaneously into the left flank of nude mice. Gene transduction efficiency was examined after a single injection of 0.1, 0.5, 1.0 and $2.5 \times 10^8$ pfu of ADV-AP into AsPC-1 subcutaneous tumors, and found that the injection of $0.1 \times 10^8$ pfu showed the transgene expression in less than 50% of the subcutaneous tumor cells, whereas intratumoral administration of more than $0.5 \times 10^8$ pfu resulted in the expression in 70-80% of the tumor cells. First, $2.5 \times 10^8$ pfu of each viral solution was injected into AsPC-1 subcutaneous tumors. The amount of virus pfu administered per mouse (one mouse weighs 25 g) may also be calculated as pfu/day/kg. Accordingly, in the specification, 0.5 to $5 \times 10^8$ pfu would be converted to 2 to $20 \times 10^9$ pfu/day/kg.

Figure 6A:
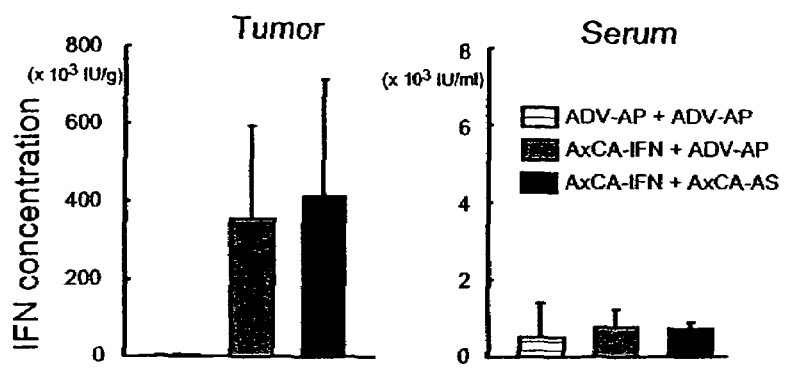
FIGS. 6a, 6b and 6c. Anti-tumor effect of the combination therapy in subcutaneous tumor model. a) IFN-α concentration in the subcutaneous tumor and the serum 3 days after the intratumoral injection of adenoviruses. IFN-α was measured by enzyme-linked immunosorbant assay (Immunotech) (n=3). b) Growth inhibition of subcutaneous tumors by a single intratumoral injection of AxCA-IFN and AxCA-AS. (Left) Total of $5.0\times10^8$ pfu ($2.5\times10^8$ pfu each) of adenoviruses was injected into tumors (n=10, ADV-AP plus ADV-AP: n=9). (Right) Total of $1.0\times10^8$ pfu ($0.5\times10^8$ pfu each) of adenoviruses was injected into tumors (n=11, ADV-AP plus ADV-AP: n=10). Tumor sizes (mean±SEM (standard error of mean)) were measured on the days indicated. c) Cell death induced by AxCA-IFN in vivo. Subcutaneous tumors were stained by ApopTag 28 days after the intratumoral injection of AxCA-IFN and ADV-AP. N: necrotic cancer tissue. V: viable cancer tissue (×200).
Figure 6B:
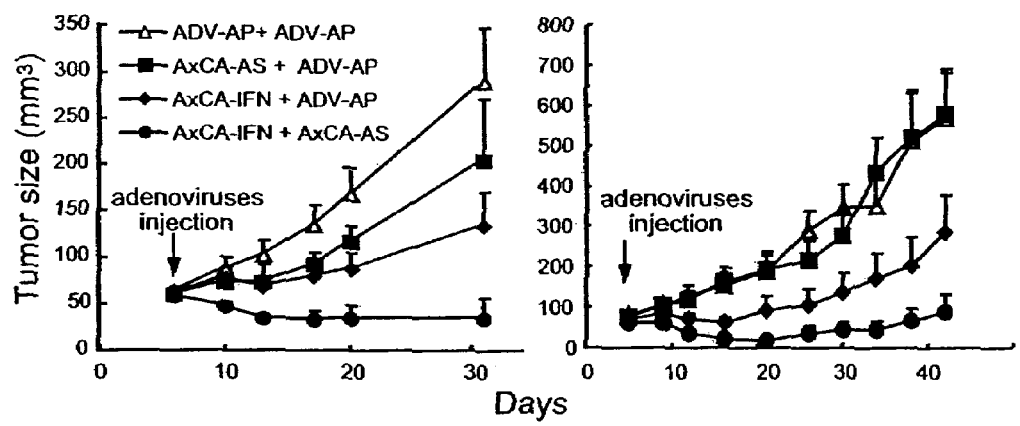
Figure 6C:
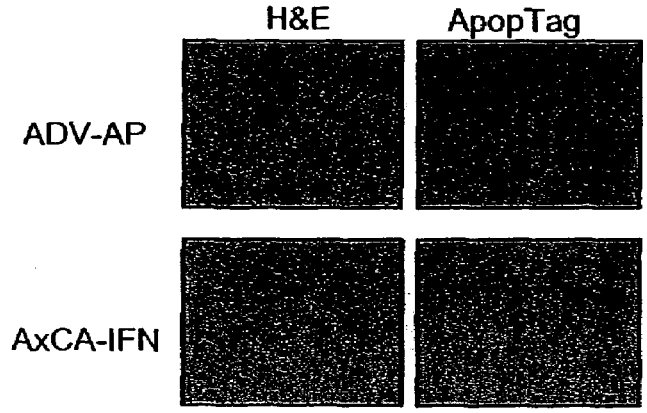

Approximately $4 \times 10^5$ IU of human IFN-α per gram of tissue was produced in the subcutaneous tumor 3 days after the injection of AxCA-IFN and/or AxCA-AS, whereas IFN-α levels in the serum of 3 groups were less than $1 \times 10^3$ IU/ml (FIG. 6a). The infection of AxCA-AS alone showed growth suppression of an AsPC-1 subcutaneous tumor, and the AxCA-IFN effectively suppressed the tumor growth (FIG. 6b, left). Histological analysis of AxCA-IFN-injected tumors revealed massive cell death and apoptosis induction (FIG. 6c), suggesting that IFN-α expression induced a significant cell death in vivo as well. The co-infection of AxCA-AS and AxCA-IFN significantly suppressed the subcutaneous tumor growth (FIG. 6b, left). Injection of the ADV-AP at the same dose had no effect on tumor growth of AsPC-1 cells, and no significant histological changes were observed in the tumor tissue. There was no pathological change in major organs such as brain, lung, heart, liver, spleen, pancreas, kidney, stomach, intestine, testis and skeletal muscle of vector-infected mice. A submaximal dose ($0.5 \times 10^8$ pfu) of each virus was used in a subcutaneous tumor model to examine the in vivo synergistic effect of the combination therapy. The injection of AxCA-AS alone did not show any growth suppression compared with the control ADV-AP, whereas its combination with AxCA-IFN significantly enhanced the antitumor effect of IFN-α expression by AxCA-IFN (FIG. 6b, right).

Example 8

Generation of Tumors at Distant Sites

Seven-to-eight-week-old female BALB/c nude mice were obtained from Charles River Japan (Kanagawa, Japan), and kept in a specific-pathogen-free environment. Among the cell lines used in this study, AsPC-1 was chosen for an in vivo gene transfer model, because the cells rapidly form a tumor when inoculated in the subcutaneous or peritoneal space of nude mice. For the peritoneal dissemination treatment, $5 \times 10^6$ cells of AsPC-1 cell suspensions were injected subcutaneously into the left leg. When the tumor mass on the left leg was established, $1 \times 10^6$ or $5 \times 10^6$ cells of AsPC-1 cell suspensions were injected into the peritoneal cavity. One day later, $1.0 \times 10^8$ pfu of the viral solution was injected once into the subcutaneous tumor, and the animals were observed for survival. Animal protocols were reviewed and approved by the Institutional Animal Core and Use Committee of the National Cancer Center Research Institute.

Example 9

Suppression of Tumors at Distant Sites by Intratumoral Injection of AdCA-mIFN

The effect of mouse IFN-α gene transduction on untreated tumors at distant sites was measured. AsPC-1 cells were injected into the left leg and the peritoneal cavity, and again, when tumor mass was established on the left leg, 1×10⁸ pfu of adenovirus was injected once into the tumor. The treatment with AdCA-mIFN resulted in a profound and statistically significant improvement (p<0.01) in the survival of the treated mice as compared with AxCA-IFN and AdCA-AP (FIG. 11). All of the dead animals were confirmed to have disseminated tumors in the peritoneal cavity. These data demonstrated that the antitumor effect of a local IFN-α gene therapy is not limited to a locally injected tumor site but that it can induce a systemic antitumor effect against pancreatic cancer cells. This systemic antitumor effect may comprise systemic immunity against pancreatic cancer cells.

Example 10

Suppression of Tumors by Activation of the Innate Immune System

In a clinical setting, IFN-alpha gene therapy may exert tumor suppressive effects based both on direct cytotoxicity and indirect immunological antitumor activities, the combination of which is expected to be highly efficacious against locally advanced pancreatic cancer. Even though some pancreatic cancer cells are resistant to the direct antiproliferation and cell death-inducing activities of IFN-alpha, such resistant cancer cells could be suppressed by activation of the innate immune system. Moreover, IFN-alpha-mediated activation of a host adaptive immune system may also contribute to the mounting of a systemic immunity against pancreatic cancer in this direct local IFN-alpha gene therapy. For example, FIG. 9 shows that when a mouse IFN-alpha is injected into a subcutaneous tumor system, natural killer cells are activated and the indirect antitumor activity is increased.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

DOCUMENTS CITED

1. Hailer D G. Future directions in the treatment of pancreatic cancer. *Seminars in Oncology* 2002; 29: 31-39.
2. Ryan D P, Willett C G. Management of locally advanced adenocarcinoma of the pancreas. *Hematol Oncol Clin North Am* 2002; 16: 95-103.
3. Kaufman H L, DiVito J, Horig H. Immunotherapy for pancreatic cancer: current concepts. *Hematol Oncol Clin North Am* 2002; 16: 159-197.
4. Pfeffer L M, et al. Biological properties of recombinant alpha-interferons: 40th anniversary of the discovery of interferons. *Cancer Res* 1998; 58: 2489-2499.
5. Gutterman J U. Cytokine therapeutics: lessons from interferon alpha. *Proc Natl Acad Sci USA* 1994; 91: 1198-1205.
6. Matsubara N, Fuchimoto S, Orita K. Antiproliferative effects of natural human tumor necrosis factor-alpha, interferon-alpha, and interferon-gamma on human pancreatic carcinoma cell lines. *Int J Pancreatol* 1991; 8: 235-243.
7. Watanabe T, et al. Anti-proliferative effect on human pancreatic cancer cells of natural human tumour necrosis factor-beta combined with natural human interferon-alpha or interferon-gamma. *J Int Med Res* 1992; 20: 112-120.
8. Recchia F, et al. Advanced carcinoma of the pancreas: phase II study of combined chemotherapy, beta-interferon, and retinoids. *Am J Clin Oncol* 1998; 21: 275-278.
9. Nukui Y, Picozzi V J, Traverso L W. Interferon-based adjuvant chemoradiation therapy improves survival after pancreaticoduodenectomy for pancreatic adenocarcinoma. *Am J Surg* 2000; 179: 367-371.
10. Macdonald J S, et al. A phase II trial of etoposide, leucovorin, 5-FU, and interferon alpha 2b (ELFI)+G-CSF for patients with pancreatic adenocarcinoma: a Southwest Oncology Group study (SWOG 9413). *Invest New Drugs* 2000; 18: 269-273.
11. David A K, et al. A phase II trial of 5-fluorouracil, leucovorin, and interferon alpha 2A (IFN-alpha 2a) in metastatic pancreatic carcinoma: a Penn Cancer Clinical Trials Group (PCCTG) trial. *Am J Clin Oncol* 2000; 23: 37-39.
12. Ahmed C M, et al. Selective expression of nonsecreted interferon by an adenoviral vector confers antiproliferative and antiviral properties and causes reduction of tumor growth in nude mice. *J Interferon Cytokine Res* 2001; 21: 399408.
13. Zhang J F, et al. Treatment of a human breast cancer xenograft with an adenovirus vector containing an interferon gene results in rapid regression due to viral oncolysis and gene therapy. *Proc Natl Acad Sci USA* 1996; 93: 4513-4518.
14. Ahmed C M, et al. In vivo tumor suppression by adenovirus-mediated interferon alpha2b gene delivery. *Hum Gene Ther* 1999; 10: 77-84.
15. Santodonato L, et al. Antitumor activity of recombinant adenoviral vectors expressing murine IFN-alpha in mice injected with metastatic IFN-resistant tumor cells. *Cancer Gene Ther* 2001; 8: 63-72.
16. Tuting T, et al. Interferon-alpha gene therapy for cancer: retroviral transduction of fibroblasts and particle-mediated transfection of tumor cells are both effective strategies for gene delivery in murine tumor models. *Gene Ther* 1997; 4: 1053-1060.
17. Mecchia M, et al. Type I consensus interferon (CIFN) gene transfer into human melanoma cells up-regulates p53 and enhances cisplatin-induced apoptosis: implications for new therapeutic strategies with IFN-alpha. *Gene Ther* 2000; 7: 167-179.
18. Coleman M, et al. Nonviral interferon alpha gene therapy inhibits growth of established tumors by eliciting a systemic immune response. *Hum Gene Ther* 1998; 9: 2223-2230.
19. Horton H M, et al. A gene therapy for cancer using intramuscular injection of plasmid DNA encoding interferon alpha. *Proc Natl Acad Sci USA* 1999; 96: 1553-1558.
20. Aoki K, Yoshida T, Sugimura T, Terada M. Liposome-mediated in vivo gene transfer of antisense K-ras construct inhibits pancreatic tumor dissemination in the murine peritoneal cavity. *Cancer Res* 1995; 55: 3810-3816.
21. Aoki K, et al. Suppression of Ki-ras p21 levels leading to growth inhibition of pancreatic cancer cell lines with Ki-ras mutation but not those without Ki-ras mutation. *Mol Carcinog* 1997; 20: 251-258.

22. Ohnami S, et al. Identification of genes showing differential expression in antisense K-ras-transduced pancreatic cancer cells with suppressed tumorigenicity. *Cancer Res* 1999; 59: 5565-5571.
23. Rebouillat D, Hovanessian A G. The human 2',5'-oligoadenylate synthetase family: interferon-induced proteins with unique enzymatic properties. *J Interferon Cytokine Res* 1999; 19: 295-308.
24. Castelli J C, et al. A study of the interferon antiviral mechanism: apoptosis activation by the 2-5A system. *J Exp Med* 1997; 186: 967-972.
25. Diaz-Guerra M, Rivas C, Esteban M. Activation of the IFN-inducible enzyme RNase L causes apoptosis of animal cells. *Virology* 1997; 236: 354-363.
26. Zhou A, et al. Interferon action and apoptosis are defective in mice devoid of 2',5'-oligoadenylate-dependent RNase L. *EMBO J.* 1997; 16: 6355-6363.
27. Ohnami S, et al. Expression profiles of pancreatic cancer cell lines infected with antisense K-ras-expressing adenoviral vector. *Biochem Biophys Res Commun* 2003; 309: 798-803.
28. Silverman R H, et al. Control of the ppp(A2'p)nA system in Hela cells: effects of interferon and virus infection. *Eur J Biochem* 1982; 124: 131-138.
29. Buechner S A, et al. Regression of basal cell carcinoma by intralesional interferon-alpha treatment is mediated by CD95 (Apo-1/Fas)-CD95 ligand-induced suicide. J Clin Invest 1997; 100: 2691-2696.
30. Lewis J A, Huq A, Najarro P. Inhibition of mitochondrial function by interferon. *J Biol Chem* 1996; 271: 13184-13190.
31. Le Roy F, et al. The 2-5A/RNase L/RNase L inhibitor (RLI) pathway regulates mitochondrial mRNAs stability in interferon alpha-treated H9 cells. *J Biol Chem* 2001; 276: 48473-48482.
32. Suzuki K, et al. Adenovirus-mediated gene transfer of interferon-α improves dimethylnitrosamine-induced liver cirrhosis in rat model. *Gene Ther* 2003; 10: 765-773.
33. Nakano M, et al. Suppression of colorectal cancer growth using an adenovirus vector expressing an antisense K-ras RNA. *Mol Ther* 2001; 3: 491-499.
34. Krasnykh V, Douglas J T. Targeted adenoviral vectors I: transductional targeting. In: Curiel D T, Douglas J T, editors. Adenoviral vectors for gene therapy. San Diego: Academic Press; 2002. p. 205-245.
35. Martell R E, Nevins J R, Sullenger B A. Optimizing aptamer activity for gene therapy applications using expression cassette SELEX. *Mol Ther* 2002; 6: 30-36.
36. Yamada H, et al. Establishment of a human pancreatic adenocarcinoma cell line (PSN-1) with amplifications of both c-myc and activated c-Ki-ras by a point mutation. *Biochem Biophys Res Commun* 1986; 140: 167-173.
37. Aoki K, et al. Efficient generation of recombinant adenoviral vectors by Cre-lox recombination in vitro. *Mol Med* 1999; 5: 224-231.
38. Player M R, et al. Ribonuclease L, a 2-5A-dependent enzyme: purification to homogeneity and assays for 2-5A binding and catalytic activity. *Methods* 1998; 15: 243-253.

The disclosure of each the above-mentioned documents 1 to 38, and of each and every document cited in the specification, is incorporated by reference herein in its entirety.

What is claimed is:

1. A method of suppressing growth of pancreatic tumors or cancer cells having a K-ras gene point mutation in a mammal, comprising: administering therapeutically effective amounts of adenoviral vector and antisense K-ras expressing vector to pancreatic cancer cells of the mammal via intratumoral administration, wherein the adenoviral vector comprises a DNA sequence encoding human IFN-alpha and operably linked to a promoter, wherein the pancreatic cancer cells to which the adenoviral vector is administered express the human IFN-alpha; and the antisense K-ras expressing vector comprises an antisense K-ras nucleotide sequence operably linked to a promoter, wherein the pancreatic cancer cells to which the anti-sense K-ras expressing vector is administered express the antisense K-ras nucleotide sequence; whereby expression of the human IFN-alpha and the antisense K-ras nucleotide sequence suppresses growth of pancreatic tumor or cancer cells in the mammal.

2. The method of claim 1, wherein the promoter of the adenoviral vector is a beta-actin promoter fused to a cytomegalovirus enhancer element.

3. The method of claim 1, wherein the promoter of the antisense K-ras expressing vector is a beta-actin promoter fused to a cytomegalovirus enhancer element.

4. The method of claim 1, wherein the adenoviral vector is administered in a dose ranging from about $5 \times 10^8$ to $25 \times 10^8$ pfu (plaque forming unit)/day/tumor weight (g).

5. The method of claim 1, wherein the antisense K-ras expressing vector is administered in a dose ranging from about $5 \times 10^8$ to $25 \times 10^8$ pfu (plaque forming unit)/day/tumor weight (g).

6. The method of claim 1, comprising administering both vectors to pancreatic cancer cells at the pancreas, administering both vectors to pancreatic cancer cells not localized at the pancreas, or a combination thereof.

7. The method of claim 1, comprising administering both vectors to pancreatic cancer cells at the pancreas, and causing regression of pancreatic cancer cells at the pancreas or regression of pancreatic cancer cells anywhere in the mammal.

8. The method of claim 1, comprising administering both vectors to pancreatic cancer cells localized distant from the pancreas, and causing regression of pancreatic cancer cells at the pancreas or pancreatic cancer cells anywhere in the mammal.

9. The method of claim 1, wherein the vectors are administered to an identifiable mass of pancreatic cancer cells not localized at the pancreas.

10. The method of claim 1, wherein an antitumor effect is observed systemically.

11. A method of inducing apoptosis in pancreatic cancer cells having a K-ras gene point mutation in a mammal comprising administering to the mammal via intratumoral administration at least one combination using two or more components with at least one component being a vector comprising a DNA sequence encoding interferon-alpha and at least one component being a vector comprising an antisense K-ras RNA nucleotide sequence.

* * * * *